US010739355B2

(12) United States Patent
Bahn et al.

(10) Patent No.: US 10,739,355 B2
(45) Date of Patent: Aug. 11, 2020

(54) SERUM BIOMARKER PANELS FOR BIPOLAR DISORDER

(71) Applicant: Cambridge Enterprise Limited, Cambridge, Cambridgeshire (GB)

(72) Inventors: Sabine Bahn, Cambridge (GB); Jason Cooper, Cambridge (GB); Frieder Haenisch, Cambridge (GB)

(73) Assignee: Cambridge Enterprise Limited, Cambridge (GB)

( * ) Notice: Subject to any disclaimer, the term of this patent is extended or adjusted under 35 U.S.C. 154(b) by 119 days.

(21) Appl. No.: 15/543,962

(22) PCT Filed: Nov. 15, 2016

(86) PCT No.: PCT/GB2016/050088
§ 371 (c)(1),
(2) Date: Jul. 14, 2017

(87) PCT Pub. No.: WO2016/113570
PCT Pub. Date: Jul. 21, 2016

(65) Prior Publication Data
US 2018/0120331 A1 May 3, 2018

(30) Foreign Application Priority Data

Jan. 16, 2015 (GB) .................................. 1500729.7

(51) Int. Cl.
*A61K 38/00* (2006.01)
*C12Q 1/68* (2018.01)
*G01N 33/567* (2006.01)
*G01N 33/68* (2006.01)

(52) U.S. Cl.
CPC ......... *G01N 33/6893* (2013.01); *G01N 33/68* (2013.01); *G01N 2333/47* (2013.01); *G01N 2333/52* (2013.01); *G01N 2333/70578* (2013.01); *G01N 2333/70596* (2013.01); *G01N 2333/96494* (2013.01); *G01N 2800/304* (2013.01); *G01N 2800/50* (2013.01); *G01N 2800/52* (2013.01); *G01N 2800/60* (2013.01)

(58) Field of Classification Search
None
See application file for complete search history.

(56) References Cited

U.S. PATENT DOCUMENTS 10,386,362 B2   8/2019   Bahn et al.

FOREIGN PATENT DOCUMENTS

WO    2016/113570    7/2016

OTHER PUBLICATIONS

Anastasia, A. et al., "Val66Met polymorphism of BDNF alters prodomain structure to induce neuronal growth cone retraction", Nature Communications, vol. 4, pp. 1-12, (2013).
As, S. et al., "A study of serum apolipoprotein A1, apolipoprotein B and lipid profile in stroke", Journal of Clinical and Diagnostic Research, vol. 7, No. 7, pp. 1303-1306, (2013).
Atluri, G. et al., "Complex biomarker discovery in neuroimaging data: Finding a needle in a haystack", NeuroImage: Clinical, vol. 3, pp. 123-131, (2013).
Bertenshaw, G.P. et al., "Multianalyte profiling of serum antigens and autoimmune and infectious disease molecules to identify biomarkers dysregulated in epithelial ovarian cancer", Cancer Epidemiol Biomarkers Prev, vol. 17, No. 10, pp. 2872-2881.
Bragazzi, N.L., "Rethinking psychiatry with OMICS science in the age of personalized P5 medicine: ready for psychiatome?", Philosophy, Ethics, and Humanities in Medicine, vol. 8, No. 4, pp. 1-7, (2013).
Carta, M.G. et al., "The risk of bipolar disorders in multiple sclerosis", Journal of Affective Disorders, vol. 155, pp. 255-260, (2014).
Chan, M.K. et al., "Applications of blood-based protein biomarker strategies in the study of psychiatric disorders", Progress in Neurobiology, vol. 122, pp. 45-72, (2014).
Chopra, K. et al., "MMPs: a novel drug target for schizophrenia", Expert Opinion Therapeutics Targets, vol. 19, No. 1, pp. 77-85, (2015).
Colom, F. et al., "The road to DSM-V, bipolar disorder episode and course specifiers", Psychopathology, vol. 42, pp. 209-218, (2009).
Colom, F. et al., "Clinical and therapeutic implications of predominant polarity in bipolar disorder", Journal of Affective Disorders, vol. 93, pp. 13-17, (2006).
Cossins, J.A. et al., "Enhanced expression of MMP-7 and MMP-9 in demyelinating multiple sclerosis lesions", Acta Neuropathologica, vol. 94, issue 6, pp. 590-598, (1997).
Craddock, N. et al., "Genetics of bipolar disorder", The Lancet, vol. 381, pp. 1654-1662, (2013).
De Peri, L. et al., "Brain structural abnormalities at the onset of schizophrenia and bipolar disorder: a meta-analysis of controlled magnetic resonance imaging studies", Current Pharmaceutical Design, vol. 18, pp. 486-494, (2012).
Friedman, J. et al., "Regularization paths for generalized linear models via coordinate descent", Journal of Statistical Software, vol. 33, issue 1, pp. 1-22, (2010).
Ghaemi, S.N. et al., "Is bipolar disorder still underdiagnosed? Are antidepressants overutilized?", Journal of Affective Disorders, vol. 52, pp. 135-144, (1999).
Goldstein, B.I. et al., "Cardiovascular disease and hypertension among adults with bipolar I disorder in the United States", Bipolar Disorder, vol. 11, No. 6, pp. 657-662, (2009).
Haenisch, F. et al., "Towards a blood-based diagnostic panel for bipolar disorder", Brain, Behavior, and Immunity, vol. 52, pp. 49-57, (2016).
Haenisch, F. et al., "Multiplex immunoassay analysis of plasma shows prominent upregulation of growth factor activity pathways linked to GSK3β signaling in bipolar patients", Journal of Affective Disorders, vol. 156, pp. 139-143, (2014).

(Continued)

*Primary Examiner* — Olga N Chernyshev
(74) *Attorney, Agent, or Firm* — Evan Law Group LLC

(57) ABSTRACT

The invention relates to biomarkers and methods of diagnosing or monitoring bipolar disorder, or a predisposition thereto.

20 Claims, 11 Drawing Sheets

(56) References Cited

OTHER PUBLICATIONS

Hashimoto, K., "Brain-derived neurotrophic factor as a biomarker for mood disorders: an historical overview and future directions", Psychiatry and Clinical Neurosciences, vol. 64, pp. 341-357, (2010).
Hirschfeld, R.M.A. et al., "Perceptions and impact of bipolar disorder: How far have we really come? Results of the national depressive and manic-depressive association 2000 survey of individuals with bipolar disorder", Journal of Clinical Psychiatry, vol. 64, pp. 161-174, (2003).
Huang, JT-J. et al., "Independent protein-profiling studies show a decrease in apolipoprotein A1 levels in schizophrenia CSF, brain and peripheral tissues", Molecular Psychiatry, vol. 13, pp. 1118-1128, (2008).
International Search Report and Written Opinion dated Apr. 11, 2016 for application PCT/GB2016/050088.
Johnson, W.E. et al., "Adjusting batch effects in microarray expression data using empirical Bayes methods", Biostatistics, vol. 8, No. 1, pp. 118-127, (2007).
Keeney, J.T.R. et al., "Apolipoprotein A-I: Insights from redox proteomics for its role in neurodegeneration", Proteomics Clinical Applications, vol. 7, pp. 109-122, (2013).
Kilbourne, A.M. et al., "Burden of general medical conditions among individuals with bipolar disorder", Bipolar Disorders, vol. 6, pp. 368-373, (2004).
Kim, Y-K. et al.,"Imbalance between pro-inflammatory and anti-inflammatory cytokines in bipolar disorder", Journal of Affective Disorders, vol. 104, pp. 91-95, (2007).
Lakka, H-M. et al., "The metabolic syndrome and total and cardiovascular disease mortality in middle-aged men", JAMA, vol. 288, No. 21, pp. 2709-2716, (2002).
Leboyer, M. et al., "Can bipolar disorder be viewed as a multisystem inflammatory disease?", Journal of Affective Disorders, vol. 141, pp. 1-10, (2012).
Leek, J.T. et al., "The sva package for removing batch effects and other unwanted variation in high-throughput experiments", Bioinformatics, vol. 28, No. 6, pp. 882-883, (2012).
Leon, A.C. et al., "Risk of suicidal behavior with antidepressants in bipolar and unipolar disorders", Journal of Clinical Psychiatry, vol. 75, No. 7, pp. 720-727, (2014).
Leppert, D. et al., "T cell gelatinases mediate basement membrane transmigration in vitro", The Journal of Immunology, vol. 154, pp. 4379-4389, (1995).
Lu, B., "Pro-region of neurotrophins: Role in synaptic modulation", Neuron, vol. 39, pp. 735-738, (2003).
Maeda, A. et al., "Matrix metalloproteinases in the normal human central nervous system, microglial nodules, and multiple sclerosis lesions", Journal of Neuropathology and Experimental Neurology, vol. 55, No. 3, pp. 300-309, (1996).
McElroy, S.L. et al., "Metabolic syndrome in bipolar disorder: a review with a focus on bipolar depression", Journal of Clinical Psychiatry, vol. 75, pp. 46-61, (2014).
Merikangas, K.R. et al., "Lifetime and 12-month prevalence of bipolar spectrum disorder in the National Comorbidity Survey replication", Archives of General Psychiatry, vol. 64, pp. 543-552, (2007).
Millikan, A.M. et al., "Evaluation of data obtained from military disability medical administrative databases for service members with schizophrenia or bipolar disorder", Military Medicine, vol. 172, pp. 1032-1038, (2007).
Müller-Oerlinghausen, B. et al., "Bipolar disorder", The Lancet, vol. 359, pp. 241-247, (2002).
Niebuhr, D.W. et al., "Association between bovine casein antibody and new onset schizophrenia among US military personnel", Schizophrenia Research, vol. 128, pp. 51-55, (2011).
Ning, M. et al., "Association between tPA therapy and raised early matrix metalloproteinase-9 in acute stroke", Neurology, vol. 66, pp. 1550-1555, (2006).
Olesen, J. et al., "The economic cost of brain disorders in Europe", European Journal of Neurology, vol. 19, pp. 155-162, (2012).
Papakostas, G.I. et al., "Assessment of a multi-assay, serum-based biological diagnostic test for major depressive disorder: a pilot and replication study", Molecular Psychiatry, vol. 18, pp. 332-339, (2013).
Paykel, E., "Manic-Depressive Illness: Bipolar Disorders and Recurrent Depression (2nd edition)", British Journal of Psychiatry, vol. 193, pp. 86-87, (2008).
Pelayo-Teran, J.M. et al., "Epidemiological factors associated with treated incidence of first-episode non-affective psychosis in cantabria: insights from the clinical programme on early phases of psychosis", Early Intervention in Psychiatry, vol. 2, pp. 178-187, (2008).
Penninx, B.W.J.H. et al., "The Netherlands study of depression and anxiety (NESDA): rationale, objectives and methods", International Journal of Methods in Psychiatric Research, vol. 17, No. 3, pp. 121-140, (2008).
Romi, F. et al., "Serum levels of matrix metalloproteinases: implications in clinical neurology", European Neurology, vol. 67, pp. 121-128, (2012).
Rosenberg, G.A. et al., "TIMP-2 reduces proteolytic opening of blood-brain barrier by type IV collagenase", Brain Research, vol. 576, pp. 203-207, (1992).
Schwarz, E. et al., "Biomarker discovery in psychiatric disorders", Electrophoresis, vol. 29, pp. 2884-2890, (2008).
Schwarz, E. et al., "Identification of a biological signature for schizophrenia in serum", Molecular Psychiatry, vol. 17, pp. 494-502, (2011).
Schwarz, E. et al., "Identification of a blood-based biological signature in subjects with psychiatric disorders prior to clinical manifestation", The World Journal of Biological Psychiatry, vol. 13, issue 8, pp. 627-632, (2012).
Schwarz, E. et al., "Validation of a blood-based laboratory test to aid in the confirmation of a diagnosis of schizophrenia", Biomarker Insights, vol. 5, pp. 39-47, (2010).
Schwarz, E. et al., "Schizophrenia Biomarkers: A means to advance disease understanding, diagnosis and treatment", Biomarkers for Psychiatric Disorders, chapter 4, pp. 75-96, (2009).
Sodersten, K. et al., "Abnormality in serum levels of mature brain-derived neurotrophic factor (BDNF) and its precursor proBDNF in mood-stabilized patients with bipolar disorder: A study of two independent cohorts", Journal of Affective Disorders, vol. 160, pp. 1-9, (2014).
Tsai, H.C. et al., "Expression of matrix metalloproteinases and their tissue inhibitors in the serum and cerebrospinal fluid of patients with meningitis", Clinical Microbiology and Infection, vol. 17, No. 5, pp. 780-784, (2011).
Vieta, E. et al., "Predominant previous polarity as an outcome predictor in a controlled treatment trial for depression in bipolar I disorder patients", Journal of Affective Disorders, vol. 119, pp. 22-27, (2009).
Waubant, E. et al., "Serum MMP-9 and TIMP-1 levels are related to MRI activity in relapsing multiple sclerosis", Neurology, vol. 53, pp. 1397-1401, (1999).
Wittchen, H.U. et al., "The size and burden of mental disorders and other disorders of the brain in Europe 2010", European Neuropsychopharmacology, vol. 21, pp. 655-679, (2011).
Ybarra, M.I. et al., "Bipolar disorder and multiple sclerosis", Arq Neuropsiquiatr, vol. 65, No. 4-B, pp. 1177-1180, (2007).
Zetterberg, H. et al., "Blood-cerebrospinal fluid barrier dysfunction in patients with bipolar disorder in relation to antipsychotic treatment", Psychiatry Research, vol. 217, pp. 143-146, (2014).
7 Pages, Jul. 18, 2017, PCT/GB2016/050088, EP.
4 Pages, Aug. 1, 2018, 16 703 600.3, EP.

SERUM BIOMARKER PANELS FOR BIPOLAR DISORDER

CROSS-REFERENCE TO RELATED APPLICATIONS

This application is a U.S. National Stage of International Patent Application No. PCT/GB2016/050088, filed Jan. 15, 2016, which claims the benefit of priority to GB Application No. 1500729.7, filed Jan. 16, 2015, each of which is incorporated herein by reference in its entirety.

FIELD OF THE INVENTION

The invention relates to biomarkers and methods of diagnosing or monitoring bipolar disorder, or a predisposition thereto.

BACKGROUND OF THE INVENTION

Bipolar disorder (BD) is a devastating mental disorder characterised by remitting and relapsing episodes of depression and (hypo)mania, which can also include psychotic symptoms such as delusions and hallucinations[1]. Disease onset is commonly in late adolescence or early adulthood, affecting men and women equally. BD has a lifetime prevalence of 1.0% for bipolar I disorder and 1.1% for bipolar II disorder[2]. When compared to the general population, BD is a life shortening condition. The higher mortality rates[3] are the result of both natural (e.g. cardiovascular disease[4,5]) and unnatural (e.g. 25%-50% of BD patients will attempt suicide[6]) causes. BD has a substantial impact on the European Union (EU) population and economy. In 2010, an estimated 3 million people (0.9% of the population) within the EU had been diagnosed with BD[7], amounting to a total cost of €21.5 billion, with the majority of costs (€18.0 billion; 83.7%) being indirect such as lost productivity (e.g. sick leave)[8].

Diagnosis is still based upon clinical interviews endeavouring to identify BD mood symptoms and patterns. In most cases, the depressive symptoms at the initial presentation of BD overlap with symptoms of major depressive disorder (MDD), whilst manic symptoms overlap with symptoms observed in schizophrenia (SCZ). This overlap of symptoms frequently results in BD being misdiagnosed leading to long delays between the onset of initial symptoms until correct diagnosis. Ghaemi et al. estimated that the average delay for BD patients to be correctly diagnosed was 7.5 years[9]. Most individuals seek psychiatric care for depressive symptoms at the onset of the disorder[10,11], which was shown to correlate with a depressive-predominant polarity[12], and 30-69% of these individuals are misdiagnosed[13]. An MDD misdiagnosis of BD patients is commonly associated with inappropriate antidepressant treatment that can precipitate hypomanic or manic symptoms, worsening the outcome for the patient. Had the individual received a correct diagnosis and been prescribed a mood stabilizer before the use of an antidepressant, their progression into hypomania or mania may have been delayed or even averted.

Despite the established clinical need for an objective test for the diagnosis of BD to be routinely used in conjunction with clinical interviews[14,15,16], extensive research into neuroimaging based biomarkers[17] and genetic risk factors (e.g. CACNA1C, ODZ4, and NCAN[18]), has as yet not resulted in a diagnostic test for routine clinical use. A proteomics based approach may prove to be more successful and has already provided promising diagnostic tests for MDD[19] and SCZ[20].

Therefore, there is a need to develop an objective test, in particular a blood-based molecular biomarker test, for identification of bipolar disorder prior to disease onset, such as prior to the onset of hypomanic or manic symptoms.

SUMMARY OF THE INVENTION

According to a first aspect of the invention, there is provided the use of a biomarker panel comprising each of the following biomarkers: CD5; Growth-Regulated alpha protein; Matrix Metalloprotease-3; Matrix Metalloprotease-7; Serum Amyloid P-component; and Tumor Necrosis Factor Receptor-Like 2; for the diagnosis or prognosis of bipolar disorder, or predisposition thereto.

According to a further aspect of the invention, there is provided the use of a biomarker panel comprising each of the following biomarkers: CD5; Growth-Regulated alpha protein; Matrix Metalloprotease-3; Matrix Metalloprotease-7; Serum Amyloid P-component; Tumor Necrosis Factor Receptor-Like 2; and CD40 ligand; for the diagnosis or prognosis of bipolar disorder, or predisposition thereto.

According to a further aspect of the invention, there is provided the use of a biomarker panel comprising each of the following biomarkers: CD5; Growth-Regulated alpha protein; Matrix Metalloprotease-3; Matrix Metalloprotease-7; Serum Amyloid P-component; Tumor Necrosis Factor Receptor-Like 2; CD40 ligand; Apolipoprotein A1 and Apolipoprotein A2; for the diagnosis or prognosis of bipolar disorder, or predisposition thereto.

According to a further aspect of the invention, there is provided the use of a biomarker panel comprising each of the following biomarkers: CD5; Growth-Regulated alpha protein; Matrix Metalloprotease-3; Matrix Metalloprotease-7; Serum Amyloid P-component; Tumor Necrosis Factor Receptor-Like 2; CD40 ligand; Apolipoprotein A1; Apolipoprotein A2; Angiotensin-Converting Enzyme; Carcinoembryonic Antigen; Cystatin C; EN-RAGE; Hepatocyte Growth Factor; Interleukin-10; Interleukin-1 receptor antagonist; Lipoprotein (a); Macrophage Inflammatory Protein-1 beta; Matrix Metalloprotease-9, total; and Receptor for advanced glycosylation end products; for the diagnosis or prognosis of bipolar disorder, or predisposition thereto.

According to a further aspect of the invention, there is provided the use of a biomarker panel comprising each of the following biomarkers: CD5; Matrix Metalloprotease-3; Matrix Metalloprotease-7; Serum Amyloid P-component; Tumor Necrosis Factor Receptor-Like 2; CD40 ligand; Apolipoprotein A1; Apolipoprotein A2; Angiotensin-Converting Enzyme; Cystatin C; EN-RAGE; Hepatocyte Growth Factor; Lipoprotein (a); Macrophage Inflammatory Protein-1 beta; Matrix Metalloprotease-9, total; and Receptor for advanced glycosylation end products; for the diagnosis or prognosis of bipolar disorder, or predisposition thereto.

According to a further aspect of the invention, there is provided the use of a biomarker panel comprising each of the following biomarkers: CD5; Matrix Metalloprotease-3; Matrix Metalloprotease-7; Serum Amyloid P-component; Tumor Necrosis Factor Receptor-Like 2; CD40 ligand; Apolipoprotein A1; Apolipoprotein A2; Angiotensin-Converting Enzyme; Cystatin C; EN-RAGE; Hepatocyte Growth Factor; Interleukin-1 receptor antagonist; Lipoprotein (a); Macrophage Inflammatory Protein-1 beta; Matrix Metalloprotease-9, total; and Receptor for advanced glycosylation end products; for the diagnosis or prognosis of bipolar disorder, or predisposition thereto.

According to a further aspect of the invention, there is provided the use of a biomarker panel comprising each of the following biomarkers: CD5; Growth-Regulated alpha protein; Matrix Metalloprotease-3; Matrix Metalloprotease-7; Serum Amyloid P-component; Tumor Necrosis Factor Receptor-Like 2; CD40 ligand; Apolipoprotein A1; Apolipoprotein A2; Angiotensin-Converting Enzyme; Carcinoembryonic Antigen; Cystatin C; EN-RAGE; Hepatocyte Growth Factor; Interleukin-1 receptor antagonist; Macrophage Inflammatory Protein-1 beta; Matrix Metalloprotease-9, total; and Receptor for advanced glycosylation end products; for the diagnosis or prognosis of bipolar disorder, or predisposition thereto.

According to a further aspect of the invention, there is provided the use of a biomarker panel comprising each of the following biomarkers: CD5; Growth-Regulated alpha protein; Matrix Metalloprotease-3; Matrix Metalloprotease-7; Serum Amyloid P-component; Tumor Necrosis Factor Receptor-Like 2; CD40 ligand; Apolipoprotein A1; Apolipoprotein A2; Angiotensin-Converting Enzyme; Carcinoembryonic Antigen; Cystatin C; EN-RAGE; Hepatocyte Growth Factor; Interleukin-1 receptor antagonist; Lipoprotein (a); Macrophage Inflammatory Protein-1 beta; Matrix Metalloprotease-9, total; and Receptor for advanced glycosylation end products; for the diagnosis or prognosis of bipolar disorder, or predisposition thereto.

According to a further aspect of the invention, there is provided a method of diagnosing bipolar disorder or predisposition in an individual thereto, comprising:
(a) quantifying the amounts of the biomarkers as defined herein in a biological sample obtained from an individual;
(b) comparing the amounts of the biomarkers in the biological sample with the amounts present in a normal control biological sample from a normal subject, such that a difference in the level of the biomarkers in the biological sample is indicative of bipolar disorder, or predisposition thereto.

According to a further aspect of the invention, there is provided a method of prognosing the development of bipolar disorder in an individual, comprising:
(a) quantifying the amounts of the biomarkers as defined herein in a biological sample obtained from an individual;
(b) comparing the amounts of the biomarkers in the biological sample with the amounts present in a normal control biological sample from a normal subject, such that a difference in the level of the biomarkers in the biological sample is indicative that the individual will develop bipolar disorder.

According to a further aspect of the invention, there is provided a method of monitoring efficacy of a therapy in a subject having, suspected of having, or of being predisposed to bipolar disorder, comprising detecting and/or quantifying, in a sample from said subject, the biomarkers as defined herein.

A further aspect of the invention provides ligands, such as naturally occurring or chemically synthesised compounds, capable of specific binding to the biomarker. A ligand according to the invention may comprise a peptide, an antibody or a fragment thereof, or an aptamer or oligonucleotide, capable of specific binding to the biomarker. The antibody can be a monoclonal antibody or a fragment thereof capable of specific binding to the biomarker. A ligand according to the invention may be labelled with a detectable marker, such as a luminescent, fluorescent or radioactive marker; alternatively or additionally a ligand according to the invention may be labelled with an affinity tag, e.g. a biotin, avidin, streptavidin or His (e.g. hexa-His) tag.

A biosensor according to the invention may comprise the biomarker or a structural/shape mimic thereof capable of specific binding to an antibody against the biomarker. Also provided is an array comprising a ligand or mimic as described herein.

Also provided by the invention is the use of one or more ligands as described herein, which may be naturally occurring or chemically synthesised, and is suitably a peptide, antibody or fragment thereof, aptamer or oligonucleotide, or the use of a biosensor of the invention, or an array of the invention, or a kit of the invention to detect and/or quantify the biomarker. In these uses, the detection and/or quantification can be performed on a biological sample such as from the group consisting of whole blood, blood serum, plasma, CSF, urine, saliva, or other bodily fluid, breath, e.g. as condensed breath, or an extract or purification therefrom, or dilution thereof.

Diagnostic, prognostic or monitoring kits are provided for performing methods of the invention. Such kits will suitably comprise a ligand according to the invention, for detection and/or quantification of the biomarker, and/or a biosensor, and/or an array as described herein, optionally together with instructions for use of the kit.

According to a further aspect of the invention, there is provided the use of a kit comprising a biosensor capable of detecting and/or quantifying the biomarkers as defined herein for monitoring, prognosing or diagnosing bipolar disorder or a predisposition thereto.

Biomarkers for bipolar disorder are essential targets for discovery of novel targets and drug molecules that retard or halt progression of the disorder. As the level of the biomarker is indicative of disorder and of drug response, the biomarker is useful for identification of novel therapeutic compounds in in vitro and/or in vivo assays. Biomarkers of the invention can be employed in methods for screening for compounds that modulate the activity of the biomarker.

Thus, in a further aspect of the invention, there is provided the use of a ligand, as described, which can be a peptide, antibody or fragment thereof or aptamer or oligonucleotide according to the invention; or the use of a biosensor according to the invention, or an array according to the invention; or a kit according to the invention, to identify a substance capable of promoting and/or of suppressing the generation of the biomarker.

Also there is provided a method of identifying a substance capable of promoting or suppressing the generation of the biomarker in a subject, comprising administering a test substance to a subject animal and detecting and/or quantifying the level of the biomarker present in a test sample from the subject.

In general, when a doctor or other medical practitioner is apprised that a patient is suffering from bipolar disorder, the practitioner will treat the individual to alleviate the causes or symptoms of the disorder. Thus, according to a further aspect of the invention, there is provided a method for treating bipolar disorder. Methods of treatment may comprise treating a patient with a bipolar disorder medicament and/or non-drug therapies. Treatment may be based upon a diagnosis or suspicion of bipolar disorder derived from the methods, biomarkers and specific panels of biomarkers as described herein.

The results of any analyses according to the invention will often be communicated to physicians and/or patients (or other interested parties such as researchers) in a transmittable form that can be communicated or transmitted to any of the above parties. Therefore, according to a further aspect of the invention, there is provided systems for diagnosing and treating bipolar disorder. These systems may comprise sample analyzers, computers and software as described herein.

DETAILED DESCRIPTION OF THE INVENTION

The results provided herein describe an extensive study which demonstrates for the first time the potential utility of the biomarker panels of the invention as a blood-based diagnostic test for BD before the development of hypomanic or manic symptoms. An early and accurate diagnosis has the potential to delay or even prevent the onset of BD.

Biomarkers

The term "biomarker" means a distinctive biological or biologically derived indicator of a process, event, or condition. Biomarkers can be used in methods of diagnosis, e.g. clinical screening, and prognosis assessment and in monitoring the results of therapy, identifying patients most likely to respond to a particular therapeutic treatment, drug screening and development. Biomarkers and uses thereof are valuable for identification of new drug treatments and for discovery of new targets for drug treatment.

Data is provided herein (in particular in Tables 5 and 6 and FIGS. 3 to 5) which demonstrates that the panels of biomarkers of the invention contain statistically significant and sensitive biomarkers for the diagnosis of bipolar disorder.

Therefore, according to a first aspect of the invention, there is provided the use of a biomarker panel comprising each of the following biomarkers: CD5; Growth-Regulated alpha protein; Matrix Metalloprotease-3; Matrix Metalloprotease-7; Serum Amyloid P-component; and Tumor Necrosis Factor Receptor-Like 2; for the diagnosis or prognosis of bipolar disorder, or predisposition thereto.

Figure 3:
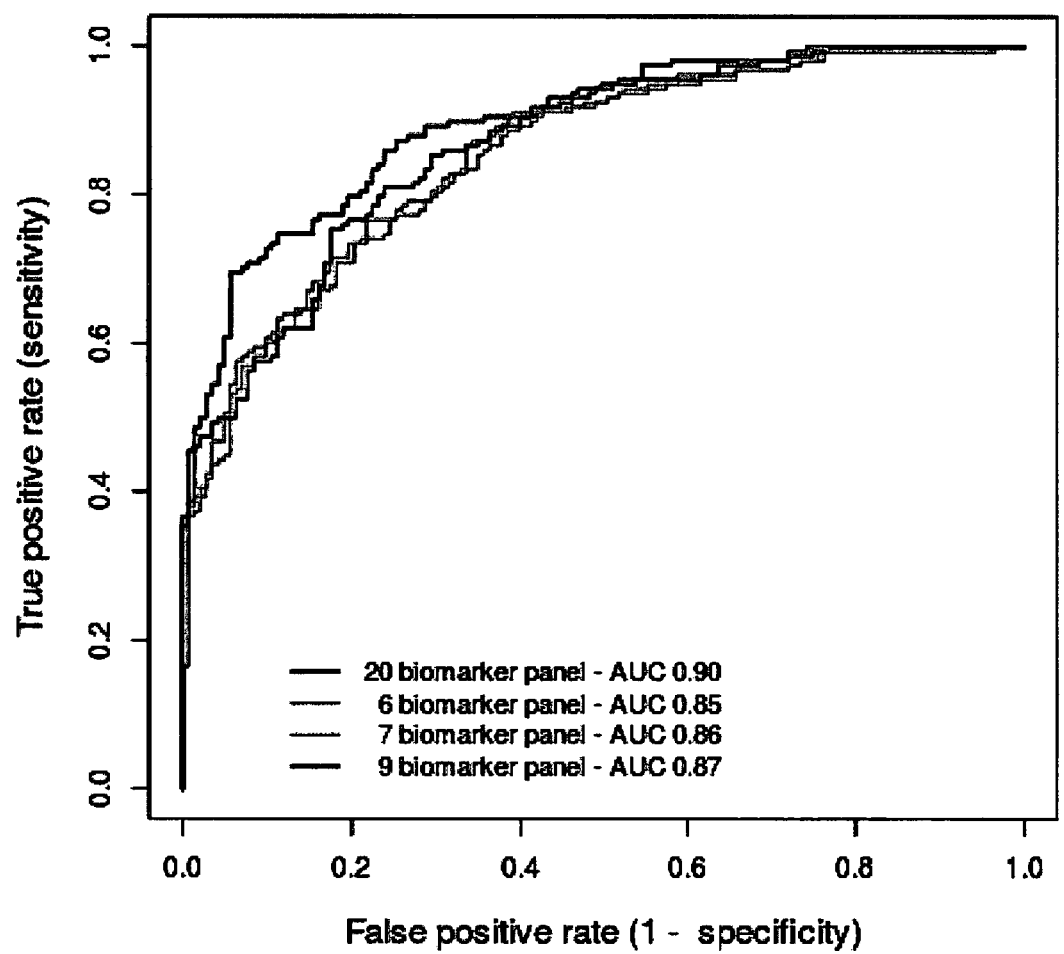
FIG. 3: Receiver operating characteristic (ROC) curves for the predictive performance of the core biomarker panels in the eight independent case-control studies used in the meta-analysis (discovery stage). AUC—area under the ROC curves.
Figure 4:
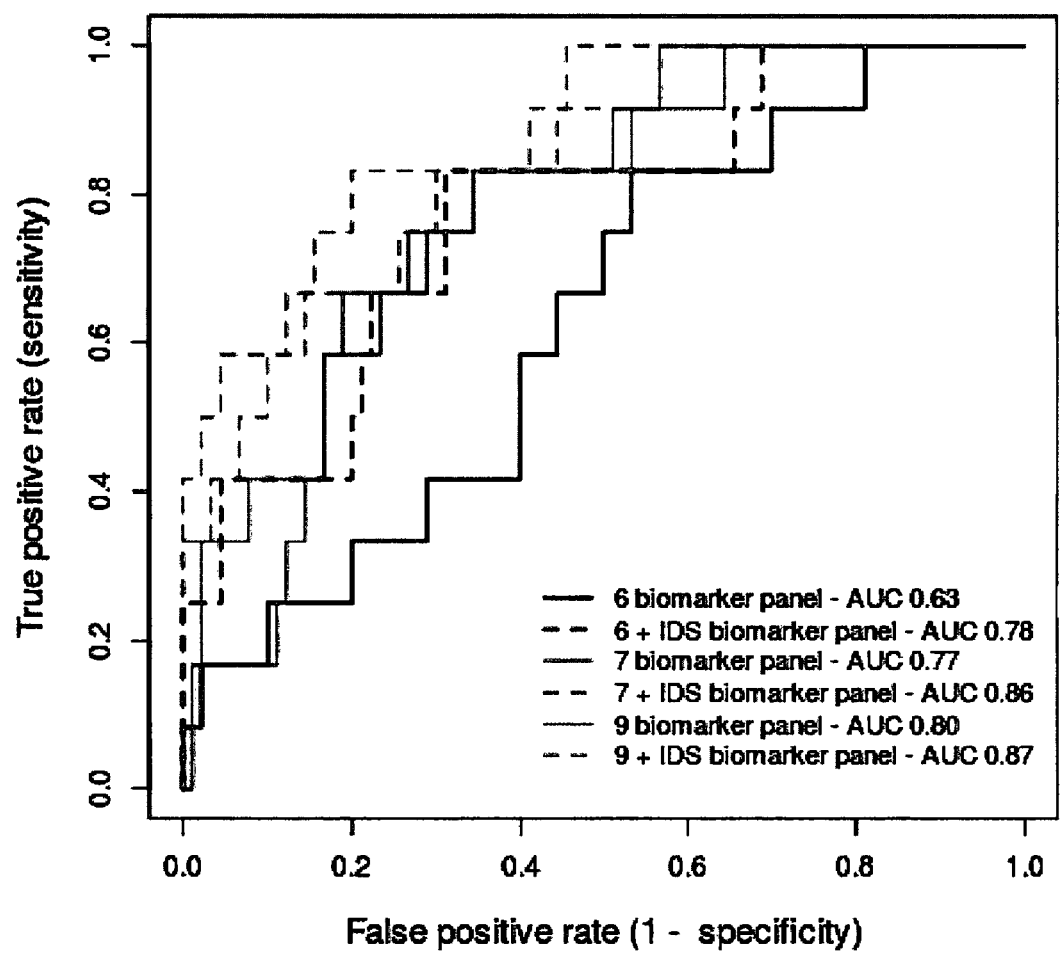
FIG. 4: Receiver operating characteristic (ROC) curves for the predictive performance of the core biomarker panels in 102 recent onset of MDD patients from NESDA, of which 12 developed BD within two years. "+IDS"=Inventory of Depressive Symptomatology score was included in the model with the biomarker panel. AUC—area under the ROC curves.
Figure 5:
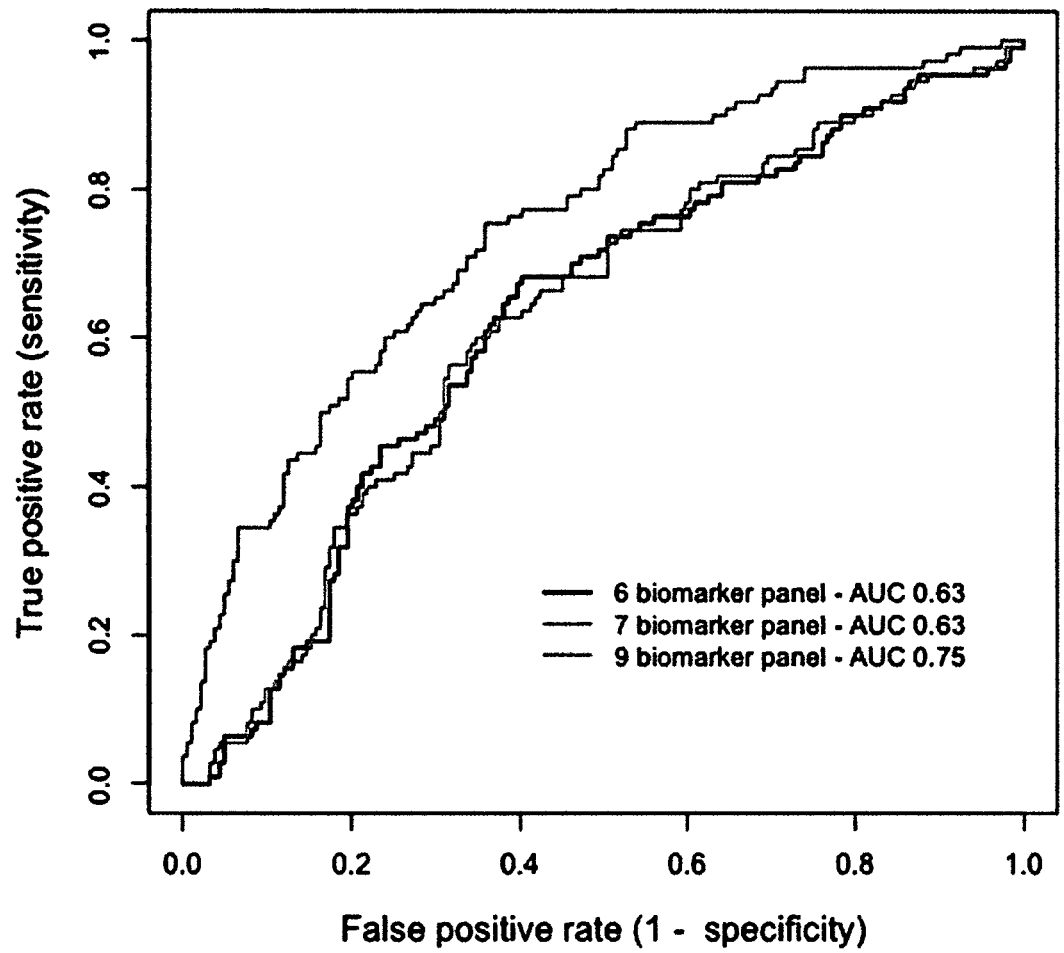
FIG. 5: Receiver operating characteristic (ROC) curves for the predictive performance of the core biomarker panels in the USA Military BD patients and controls. AUC—area under the ROC curves.

Data is provided herein which demonstrates that this panel of six biomarkers is successful at specifically and sensitively diagnosing bipolar disorder patients in most studies (see Tables 5 and 6 and FIGS. 3 to 5).

In one embodiment, the panel additionally comprises CD40 ligand. Data is provided herein which demonstrates that the addition of CD40 to the panel of six biomarkers improved the results observed for the six biomarker panel in recent onset major depressive disorder (MDD) patients from NESDA, which included patients that developed BD within two years (see Tables 5 and 6 and FIGS. 3 to 5).

Therefore, according to a further aspect of the invention, there is provided the use of a biomarker panel comprising each of the following biomarkers: CD5; Growth-Regulated alpha protein; Matrix Metalloprotease-3; Matrix Metalloprotease-7; Serum Amyloid P-component; Tumor Necrosis Factor Receptor-Like 2; and CD40 ligand; for the diagnosis or prognosis of bipolar disorder, or predisposition thereto.

In one embodiment, the panel additionally comprises Apolipoprotein A1 and Apolipoprotein A2. Data is provided herein which demonstrates that the addition of Apolipoprotein A1 and Apolipoprotein A2 to the panel of seven biomarkers improved the results observed for the seven biomarker panel in pre-symptomatic bipolar disorder patients and controls from the USA Military (see Tables 5 and 6 and FIGS. 3 to 5).

Therefore, according to a further aspect of the invention, there is provided the use of a biomarker panel comprising each of the following biomarkers: CD5; Growth-Regulated alpha protein; Matrix Metalloprotease-3; Matrix Metalloprotease-7; Serum Amyloid P-component; Tumor Necrosis Factor Receptor-Like 2; CD40 ligand; Apolipoprotein A1 and Apolipoprotein A2; for the diagnosis or prognosis of bipolar disorder, or predisposition thereto.

In one embodiment, the panel additionally comprises one or more biomarkers selected from: Angiotensin-Converting Enzyme; Carcinoembryonic Antigen; Cystatin C; EN-RAGE; Hepatocyte Growth Factor; Interleukin-10; Interleukin-1 receptor antagonist; Lipoprotein (a); Macrophage Inflammatory Protein-1 beta; Matrix Metalloprotease-9, total; and Receptor for advanced glycosylation end products.

Therefore, according to a further aspect of the invention, there is provided the use of a biomarker panel comprising each of the following biomarkers: CD5; Growth-Regulated alpha protein; Matrix Metalloprotease-3; Matrix Metalloprotease-7; Serum Amyloid P-component; Tumor Necrosis Factor Receptor-Like 2; CD40 ligand; Apolipoprotein A1; Apolipoprotein A2; Angiotensin-Converting Enzyme; Carcinoembryonic Antigen; Cystatin C; EN-RAGE; Hepatocyte Growth Factor; Interleukin-10; Interleukin-1 receptor antagonist; Lipoprotein (a); Macrophage Inflammatory Protein-1 beta; Matrix Metalloprotease-9, total; and Receptor for advanced glycosylation end products; for the diagnosis or prognosis of bipolar disorder, or predisposition thereto.

The present study (see Example 1 in particular) has identified and validated a biomarker panel of the above mentioned 20 biomarkers which demonstrated excellent predictive performance [area under the curve (AUC)≥0.90]. Importantly, the panel had a good predictive performance (AUC 0.84) to differentiate between first onset MDD patients and individuals who later develop BD, and a fair predictive performance (AUC 0.79) to differentiate between pre-symptomatic BD and controls. The present study has also demonstrated the disease specificity of the 20 biomarker panel.

In one embodiment, the twenty biomarker panel does not contain Interleukin-10. Therefore, according to a further aspect of the invention, there is provided the use of a biomarker panel comprising each of the following biomarkers: CD5; Growth-Regulated alpha protein; Matrix Metalloprotease-3; Matrix Metalloprotease-7; Serum Amyloid P-component; Tumor Necrosis Factor Receptor-Like 2; CD40 ligand; Apolipoprotein A1; Apolipoprotein A2; Angiotensin-Converting Enzyme; Carcinoembryonic Antigen; Cystatin C; EN-RAGE; Hepatocyte Growth Factor; Interleukin-1 receptor antagonist; Lipoprotein (a); Macrophage Inflammatory Protein-1 beta; Matrix Metalloprotease-9, total; and Receptor for advanced glycosylation end products; for the diagnosis or prognosis of bipolar disorder, or predisposition thereto.

In one embodiment, the twenty biomarker panel does not contain Interleukin-10 and Lipoprotein (a). Therefore, according to a further aspect of the invention, there is provided the use of a biomarker panel comprising each of the following biomarkers: CD5; Growth-Regulated alpha protein; Matrix Metalloprotease-3; Matrix Metalloprotease-7; Serum Amyloid P-component; Tumor Necrosis Factor Receptor-Like 2; CD40 ligand; Apolipoprotein A1; Apolipoprotein A2; Angiotensin-Converting Enzyme; Carcinoembryonic Antigen; Cystatin C; EN-RAGE; Hepatocyte Growth Factor; Interleukin-1 receptor antagonist; Macrophage Inflammatory Protein-1 beta; Matrix Metalloprotease-9, total; and Receptor for advanced glycosylation end products; for the diagnosis or prognosis of bipolar disorder, or predisposition thereto.

In one embodiment, the twenty biomarker panel does not contain Interleukin-10, Growth-Regulated alpha protein and Carcinoembryonic Antigen. Therefore, according to a further aspect of the invention, there is provided the use of a biomarker panel comprising each of the following biomarkers: CD5; Matrix Metalloprotease-3; Matrix Metalloprotease-7; Serum Amyloid P-component; Tumor Necrosis Factor Receptor-Like 2; CD40 ligand; Apolipoprotein A1; Apolipoprotein A2; Angiotensin-Converting Enzyme; Cystatin C; EN-RAGE; Hepatocyte Growth Factor; Interleukin-1 receptor antagonist; Lipoprotein (a); Macrophage Inflammatory Protein-1 beta; Matrix Metalloprotease-9, total; and Receptor for advanced glycosylation end products; for the diagnosis or prognosis of bipolar disorder, or predisposition thereto.

In one embodiment, the twenty biomarker panel does not contain Interleukin-10, Growth-Regulated alpha protein, Carcinoembryonic Antigen and Interleukin-1 receptor antagonist. Therefore, according to a further aspect of the invention, there is provided the use of a biomarker panel comprising each of the following biomarkers: CD5; Matrix Metalloprotease-3; Matrix Metalloprotease-7; Serum Amyloid P-component; Tumor Necrosis Factor Receptor-Like 2; CD40 ligand; Apolipoprotein A1; Apolipoprotein A2; Angiotensin-Converting Enzyme; Cystatin C; EN-RAGE; Hepatocyte Growth Factor; Lipoprotein (a); Macrophage Inflammatory Protein-1 beta; Matrix Metalloprotease-9, total; and Receptor for advanced glycosylation end products; for the diagnosis or prognosis of bipolar disorder, or predisposition thereto.

Differential Diagnosis

The results presented herein have also demonstrated that the biomarker panels described herein have high specificity for bipolar disorder. In particular, the results shown in Example 1 identified that when the twenty biomarker panel was applied to differentiate between first onset major depressive disorder (MDD) patients and individuals who later develop hypomanic or manic symptoms, good predictive performance was achieved (AUC=0.84).

Therefore, according to a further aspect of the invention, the biomarker panels described herein may be used as a panel of biomarkers for the differential diagnosis of bipolar disorder from a further psychiatric disorder, such as MDD, in particular first onset MDD. This aspect of the invention has the advantage of being able to diagnose whether MDD patients, in particular first onset MDD patients, are likely to develop full bipolar disorders prior to their first hypomanic or manic symptoms.

It will be appreciated that the term "differential diagnosis" refers to the positive diagnosis of bipolar disorder from that of a further psychiatric disorder, such as MDD, in particular first onset MDD.

Non-limiting examples of psychiatric disorders include: mood disorders such as depression, major depressive disorder, treatment resistant depression, mania, cyclothymic disorder and bipolar disorders (including bipolar disorder in manic, depressive and euthymic phases); anxiety disorders such as generalized anxiety disorder, obsessive-compulsive disorder (OCD), panic attacks and panic disorder, phobic disorders, stress disorders; dissociative disorders such as depersonalization disorder, dissociative amnesia, dissociative fugue, dissociative identity disorder; drug use and dependence; eating disorders such as anorexia nervosa, binge eating disorder and bulimia nervosa; personality disorders; sexuality and sexual disorders such as gender identity disorder and transsexualism and paraphilias; somatoform and factitious disorders such as body dysmorphic disorder, conversion disorder, hypochondriasis, Munchausen syndrome, pain disorder and somatization disorder; Asperger syndrome or suicidal behavior.

Methods of Diagnosis, Prognosis or Monitoring

According to a further aspect of the invention, there is provided a method of diagnosing bipolar disorder or predisposition in an individual thereto, comprising:
(a) quantifying the amounts of the biomarkers as defined herein in a biological sample obtained from an individual;
(b) comparing the amounts of the biomarkers in the biological sample with the amounts present in a normal control biological sample from a normal subject, such that a difference in the level of the biomarkers in the biological sample is indicative of bipolar disorder, or predisposition thereto.

According to a further aspect of the invention, there is provided a method of prognosing the development of bipolar disorder in an individual, comprising:
(a) quantifying the amounts of the biomarkers as defined herein in a biological sample obtained from an individual;
(b) comparing the amounts of the biomarkers in the biological sample with the amounts present in a normal control biological sample from a normal subject, such that a difference in the level of the biomarkers in the biological sample is indicative that the individual will develop bipolar disorder.

It should be noted that references to biomarker amounts or levels also include references to a biomarker range.

It will be appreciated that references herein to "difference in the level" refer to either a higher or lower level of the biomarker(s) in the test biological sample compared with the reference sample(s).

In one embodiment, the higher or lower level is a <1 fold difference relative to the reference sample, such as a fold difference of 0.9, 0.8, 0.7, 0.6, 0.5, 0.4, 0.3, 0.2, 0.1, 0.05, 0.01 or any ranges therebetween. In one embodiment, the lower level is between a 0.1 and 0.9 fold difference, such as between a 0.2 and 0.5 fold difference, relative to the reference sample.

In one embodiment, the higher or lower level is a >1 fold difference relative to the reference sample, such as a fold difference of 1.5, 2.0, 2.5, 3.0, 3.5, 4.0, 4.5, 5.0, 5.5, 6.0, 6.5, 7.0, 7.5, 8.0, 8.5, 9.0, 9.5, 10, 10.5, 11, 11.5, 12, 12.5, 15 or 20 or any ranges therebetween. In one embodiment, the higher level is between a 1 and 15 fold difference, such as between a 2 and 10 fold difference, relative to the reference sample.

In one embodiment, the individual is a drug naïve MDD patient (e.g. a first onset drug-naïve patient). In a further embodiment, the individual is first-onset or recent-onset drug naïve MDD patient. In a yet further embodiment, the individual is an un-medicated MDD patient. In a yet further embodiment, the individual is an individual who has not yet experienced a hypomanic or manic episode. It will be appreciated that the monitoring aspects of the invention will typically involve an individual previously diagnosed as having bipolar disorder.

It will be understood that the term "drug naïve" patients includes patients which have not previously been diagnosed or medicated for bipolar disorder. It will also be understood that the term "un-medicated" refers to patients which have not been taking medication for bipolar disorder (i.e. anti-psychiatric or anti-psychotic medication) for at least 1 year, for example for at least 2, 3, 4, 5, 6, 7, 8, 9 or 10 years, in particular for at least 3 years.

References to "bipolar disorder" as used herein refer to a mental disorder characterised by remitting and relapsing episodes of depression and (hypo)mania, which can also include psychotic symptoms such as delusions and hallucinations. References herein to bipolar disorder are intended to include both bipolar disorder I (where there has been at least one manic episode) and bipolar disorder II (where there has been at least one hypomanic episode and one major depressive episode).

According to a further aspect of the invention, there is provided a method of monitoring efficacy of a therapy in a subject having, suspected of having, or of being predisposed to bipolar disorder, comprising detecting and/or quantifying, in a sample from said subject, the biomarkers as defined herein.

Monitoring methods of the invention can be used to monitor onset, progression, stabilisation, amelioration and/or remission.

In methods of diagnosing, prognosing or monitoring according to the invention, detecting and/or quantifying the biomarker in a biological sample from a test subject may be performed on two or more occasions. Comparisons may be made between the level of biomarker in samples taken on two or more occasions. Assessment of any change in the level of the biomarker in samples taken on two or more occasions may be performed. Modulation of the biomarker level is useful as an indicator of the state of bipolar disorder or predisposition thereto. An increase in the level of the biomarker, over time is indicative of onset or progression, i.e. worsening of this disorder, whereas a decrease in the level of the biomarker indicates amelioration or remission of the disorder, or vice versa.

A method of diagnosis or prognosis of or monitoring according to the invention may comprise quantifying the biomarker in a test biological sample from a test subject and comparing the level of the biomarker present in said test sample with one or more controls.

The control used in a method of the invention can be one or more control(s) selected from the group consisting of: the level of biomarker found in a normal control sample from a normal subject, a normal biomarker level; a normal biomarker range, the level in a sample from a subject with bipolar disorder, or a diagnosed predisposition thereto; bipolar disorder biomarker level, or bipolar disorder biomarker range.

Also provided is a method of monitoring efficacy of a therapy for bipolar disorder in a subject having such a disorder, suspected of having such a disorder, or of being predisposed thereto, comprising detecting and/or quantifying the biomarker present in a biological sample from said subject. In monitoring methods, test samples may be taken on two or more occasions. The method may further comprise comparing the level of the biomarker present in the test sample with one or more reference(s) and/or with one or more previous test sample(s) taken earlier from the same test subject, e.g. prior to commencement of therapy, and/or from the same test subject at an earlier stage of therapy. The method may comprise detecting a change in the level of the biomarker in test samples taken on different occasions.

In one embodiment, the method comprises comparing the amount of biomarker(s) in said test biological sample with the amount present in one or more samples taken from said individual prior to commencement of treatment, and/or one or more samples taken from said individual during treatment.

For biomarkers which are increased in individuals with bipolar disorder, a higher level of the biomarker in the test sample relative to the level in the normal control is indicative of the presence of bipolar disorder, or predisposition thereto; an equivalent or lower level of the biomarker in the test sample relative to the normal control is indicative of absence of bipolar disorder and/or absence of a predisposition thereto. Examples of the biomarkers of the invention which have a higher level compared with the reference sample are described in Table 4 and include: Carcinoembryonic Antigen (CEA); EN-RAGE; Macrophage Inflammatory Protein-1 beta (MIP-1 beta); Serum Amyloid P-Component; Tumor Necrosis Factor Receptor-Like 2; Interleukin-1 receptor antagonist; Interleukin-10; Lipoprotein (a); Matrix Metalloprotease-7; Matrix Metalloprotease-9, total; Cystatin C; and Hepatocyte Growth Factor.

For biomarkers which are decreased in individuals with bipolar disorder, a lower level of the biomarker in the test sample relative to the level in the normal control is indicative of the presence of bipolar disorder, or predisposition thereto; an equivalent or lower level of the biomarker in the test sample relative to the normal control is indicative of absence of bipolar disorder and/or absence of a predisposition thereto. Examples of the biomarkers of the invention which have a lower level compared with the reference sample are described in Table 4 and include: CD40 ligand; Growth-Regulated alpha protein; Receptor for advanced glycosylation end products; CD5; Apolipoprotein A1; Apolipoprotein A2; Angiotensin-Converting Enzyme (ACE); and Matrix Metalloprotease-3.

The term "diagnosis" as used herein encompasses identification, confirmation, and/or characterisation of bipolar disorder, or predisposition thereto. The term "prognosis" as used herein encompasses the prediction of whether a patient it likely to develop bipolar disorder. By "predisposition" it is meant that a subject does not currently present with the disorder, but is liable to be affected by the disorder in time, for example, develop the hypomanic or manic episodes typically characterised by bipolar disorder.

Methods of monitoring and of diagnosis or prognosis according to the invention are useful to confirm the existence of a disorder, or predisposition thereto; to monitor development of the disorder by assessing onset and progression, or to assess amelioration or regression of the disorder. Methods of monitoring and of diagnosis or prognosis are also useful in methods for assessment of clinical screening, choice of therapy, evaluation of therapeutic benefit, i.e. for drug screening and drug development.

Efficient diagnosis, prognosis and monitoring methods provide very powerful "patient solutions" with the potential for improved prognosis, by establishing the correct diagnosis, allowing rapid identification of the most appropriate treatment (thus lessening unnecessary exposure to harmful drug side effects), reducing "down-time" and relapse rates.

Methods for monitoring efficacy of a therapy can be used to monitor the therapeutic effectiveness of existing therapies and new therapies in human subjects and in non-human animals (e.g. in animal models). These monitoring methods can be incorporated into screens for new drug substances and combinations of substances.

Suitably, the time elapsed between taking samples from a subject undergoing diagnosis or monitoring will be 3 days, 5 days, a week, two weeks, a month, 2 months, 3 months, 6 or 12 months. Samples may be taken prior to and/or during and/or following therapy for bipolar disorder. Samples can be taken at intervals over the remaining life, or a part thereof, of a subject.

The term "detecting" as used herein means confirming the presence of the biomarker present in the sample. Quantifying the amount of the biomarker present in a sample may include determining the concentration of the biomarker present in the sample. Detecting and/or quantifying may be performed directly on the sample, or indirectly on an extract therefrom, or on a dilution thereof.

In alternative aspects of the invention, the presence of the biomarker is assessed by detecting and/or quantifying antibody or fragments thereof capable of specific binding to the biomarker that are generated by the subject's body in response to the biomarker and thus are present in a biological sample from a subject having bipolar disorder or a predisposition thereto.

Detecting and/or quantifying can be performed by any method suitable to identify the presence and/or amount of a specific biomarker in a biological sample from a patient or a purification or extract of a biological sample or a dilution thereof. In methods of the invention, quantifying may be performed by measuring the concentration of the biomarker in the sample or samples. Biological samples that may be tested in a method of the invention include whole blood, blood serum, plasma, cerebrospinal fluid (CSF), urine, saliva, or other bodily fluid (stool, tear fluid, synovial fluid, sputum), breath, e.g. as condensed breath, or an extract or purification therefrom, or dilution thereof. Biological samples also include tissue homogenates, tissue sections and biopsy specimens from a live subject, or taken post-mortem. The samples can be prepared, for example where appropriate diluted or concentrated, and stored in the usual manner. IT will be understood that methods of the invention may be performed in vitro.

In one embodiment, the biological sample is whole blood, blood serum or plasma, such as blood serum.

Detection and/or quantification of biomarkers may be performed by detection of the biomarker or of a fragment thereof, e.g. a fragment with C-terminal truncation, or with N-terminal truncation. Fragments are suitably greater than 4 amino acids in length, for example 5, 6, 7, 8, 9, 10, 11, 12, 13, 14, 15, 16, 17, 18, 19, or 20 amino acids in length.

In one embodiment, the biomarker defined herein may be replaced by a molecule, or a measurable fragment of the molecule, found upstream or downstream of the biomarker in a biological pathway.

Methods of Detection

As used herein, the term "biosensor" means anything capable of detecting the presence of the biomarker. Examples of biosensors are described herein.

Biosensors according to the invention may comprise a ligand or ligands, as described herein, capable of specific binding to the biomarker. Such biosensors are useful in detecting and/or quantifying a biomarker of the invention.

The biomarker may be directly detected, e.g. by SELDI or MALDI-TOF. Alternatively, the biomarker may be detected directly or indirectly via interaction with a ligand or ligands such as an antibody or a biomarker-binding fragment thereof, or other peptide, or ligand, e.g. aptamer, or oligonucleotide, capable of specifically binding the biomarker. The ligand may possess a detectable label, such as a luminescent, fluorescent or radioactive label, and/or an affinity tag.

For example, detecting and/or quantifying can be performed by one or more method(s) selected from the group consisting of: SELDI (-TOF), MALDI (-TOF), a 1-D gel-based analysis, a 2-D gel-based analysis, mass spectroscopy (MS) such as selected reaction monitoring (SRM), reverse phase (RP) LC, size permeation (gel filtration), ion exchange, affinity, HPLC, UPLC and other LC or LC MS-based techniques. Appropriate LC MS techniques include ICAT® (Applied Biosystems, CA, USA), or iTRAQ® (Applied Biosystems, CA, USA). Liquid chromatography (e.g. high pressure liquid chromatography (HPLC) or low pressure liquid chromatography (LPLC)), thin-layer chromatography, NMR (nuclear magnetic resonance) spectroscopy could also be used.

In one embodiment, the detecting and/or quantifying is performed using mass spectroscopy (MS). In a further embodiment, the detecting and/or quantifying is performed using selected reaction monitoring (SRM). SRM is a method used in tandem mass spectrometry in which an ion of a particular mass is selected in the first stage of a tandem mass spectrometer and an ion product of a fragmentation reaction of the precursor ion is selected in the second mass spectrometer stage for detection. Specific analyte panels can be developed for SRM matching the analytes on the biomarker panel. The analyte panels can quantitatively measure the protein analytes with high precision. This methodology has the advantage of allowing raw blood to be used instead of blood serum which minimizes the number intermediate processing steps.

Methods according to the invention may comprise analysing a sample of blood serum by SELDI-TOF or MALDI-TOF to detect the presence or level of the biomarker. These methods are also suitable for clinical screening, prognosis, monitoring the results of therapy, identifying patients most likely to respond to a particular therapeutic treatment, for drug screening and development, and identification of new targets for drug treatment.

Detecting and/or quantifying the biomarkers may be performed using an immunological method, involving an antibody, or a fragment thereof capable of specific binding to the biomarker. Suitable immunological methods include sandwich immunoassays, such as sandwich ELISA, in which the detection of the biomarkers is performed using two antibodies which recognize different epitopes on a biomarker; radioimmunoassays (RIA), direct, indirect or competitive enzyme linked immunosorbent assays (ELISA), enzyme immunoassays (EIA), Fluorescence immunoassays (FIA), western blotting, immunoprecipitation and any particle-based immunoassay (e.g. using gold, silver, or latex particles, magnetic particles, or Q-dots). Immunological methods may be performed, for example, in microtitre plate or strip format.

Immunological methods in accordance with the invention may be based, for example, on any of the following methods.

Immunoprecipitation is the simplest immunoassay method; this measures the quantity of precipitate, which forms after the reagent antibody has incubated with the sample and reacted with the target antigen present therein to form an insoluble aggregate. Immunoprecipitation reactions may be qualitative or quantitative.

In particle immunoassays, several antibodies are linked to the particle, and the particle is able to bind many antigen molecules simultaneously. This greatly accelerates the speed of the visible reaction. This allows rapid and sensitive detection of the biomarker.

In immunonephelometry, the interaction of an antibody and target antigen on the biomarker results in the formation of immune complexes that are too small to precipitate. However, these complexes will scatter incident light and this can be measured using a nephelometer. The antigen, i.e. biomarker, concentration can be determined within minutes of the reaction.

Radioimmunoassay (RIA) methods employ radioactive isotopes such as $1^{125}$ to label either the antigen or antibody. The isotope used emits gamma rays, which are usually measured following removal of unbound (free) radiolabel. The major advantages of RIA, compared with other immunoassays, are higher sensitivity, easy signal detection, and well-established, rapid assays. The major disadvantages are the health and safety risks posed by the use of radiation and the time and expense associated with maintaining a licensed radiation safety and disposal program. For this reason, RIA has been largely replaced in routine clinical laboratory practice by enzyme immunoassays.

Enzyme (EIA) immunoassays were developed as an alternative to radioimmunoassays (RIA). These methods use an enzyme to label either the antibody or target antigen. The sensitivity of EIA approaches that of RIA, without the danger posed by radioactive isotopes. One of the most widely used EIA methods for detection is the enzyme-linked immunosorbent assay (ELISA). ELISA methods may use two antibodies one of which is specific for the target antigen and the other of which is coupled to an enzyme, addition of the substrate for the enzyme results in production of a chemiluminescent or fluorescent signal.

Fluorescent immunoassay (FIA) refers to immunoassays which utilize a fluorescent label or an enzyme label which acts on the substrate to form a fluorescent product. Fluorescent measurements are inherently more sensitive than colorimetric (spectrophotometric) measurements. Therefore, FIA methods have greater analytical sensitivity than EIA methods, which employ absorbance (optical density) measurement.

Chemiluminescent immunoassays utilize a chemiluminescent label, which produces light when excited by chemical energy; the emissions are measured using a light detector.

Immunological methods according to the invention can thus be performed using well-known methods. Any direct (e.g., using a sensor chip) or indirect procedure may be used in the detection of the biomarker of the invention.

The Biotin-Avidin or Biotin-Streptavidin systems are generic labelling systems that can be adapted for use in immunological methods of the invention. One binding partner (hapten, antigen, ligand, aptamer, antibody, enzyme etc) is labelled with biotin and the other partner (surface, e.g. well, bead, sensor etc) is labelled with avidin or streptavidin. This is conventional technology for immunoassays, gene probe assays and (bio)sensors, but is an indirect immobilisation route rather than a direct one. For example a biotinylated ligand (e.g. antibody or aptamer) specific for a biomarker of the invention may be immobilised on an avidin or streptavidin surface, the immobilised ligand may then be exposed to a sample containing or suspected of containing the biomarker in order to detect and/or quantify a biomarker of the invention. Detection and/or quantification of the immobilised antigen may then be performed by an immunological method as described herein.

The term "antibody" as used herein includes, but is not limited to: polyclonal, monoclonal, bispecific, humanised or chimeric antibodies, single chain antibodies, Fab fragments and $F(ab')_2$ fragments, fragments produced by a Fab expression library, anti-idiotypic (anti-Id) antibodies and epitope-binding fragments of any of the above. The term "antibody" as used herein also refers to immunoglobulin molecules and immunologically-active portions of immunoglobulin molecules, i.e., molecules that contain an antigen binding site that specifically binds an antigen. The immunoglobulin molecules of the invention can be of any class (e.g., IgG, IgE, IgM, IgD and IgA) or subclass of immunoglobulin molecule.

The identification of key biomarkers specific to a disease is central to integration of diagnostic procedures and therapeutic regimes. Using predictive biomarkers, appropriate diagnostic tools such as biosensors can be developed, accordingly, in methods and uses of the invention, detecting and quantifying can be performed using a biosensor, microanalytical system, microengineered system, microseparation system, immunochromatography system or other suitable analytical devices. The biosensor may incorporate an immunological method for detection of the biomarker, electrical, thermal, magnetic, optical (e.g. hologram) or acoustic technologies. Using such biosensors, it is possible to detect the target biomarker at the anticipated concentrations found in biological samples.

Thus, according to a further aspect of the invention there is provided an apparatus for monitoring bipolar disorder, which comprises a biosensor, microanalytical, microengineered, microseparation and/or immunochromatography system configured to detect and/or quantify the biomarker defined herein.

The biomarker of the invention can be detected using a biosensor incorporating technologies based on "smart" holograms, or high frequency acoustic systems, such systems are particularly amenable to "bar code" or array configurations.

In smart hologram sensors (Smart Holograms Ltd, Cambridge, UK), a holographic image is stored in a thin polymer film that is sensitised to react specifically with the biomarker. On exposure, the biomarker reacts with the polymer leading to an alteration in the image displayed by the hologram. The test result read-out can be a change in the optical brightness, image, colour and/or position of the image. For qualitative and semi-quantitative applications, a sensor hologram can be read by eye, thus removing the need for detection equipment. A simple colour sensor can be used to read the signal when quantitative measurements are required. Opacity or colour of the sample does not interfere with operation of the sensor. The format of the sensor allows multiplexing for simultaneous detection of several substances. Reversible and irreversible sensors can be designed to meet different requirements, and continuous monitoring of a particular biomarker of interest is feasible.

Suitably, biosensors for detection of the biomarker of the invention combine biomolecular recognition with appropriate means to convert detection of the presence, or quantitation, of the biomarker in the sample into a signal. Biosensors can be adapted for "alternate site" diagnostic testing, e.g. in the ward, outpatients' department, surgery, home, field and workplace.

Biosensors to detect the biomarker of the invention include acoustic, plasmon resonance, holographic and microengineered sensors. Imprinted recognition elements, thin film transistor technology, magnetic acoustic resonator devices and other novel acousto-electrical systems may be employed in biosensors for detection of the biomarker of the invention.

Methods involving detection and/or quantification of the biomarker of the invention can be performed on bench-top instruments, or can be incorporated onto disposable, diagnostic or monitoring platforms that can be used in a non-laboratory environment, e.g. in the physician's office or at the patient's bedside. Suitable biosensors for performing methods of the invention include "credit" cards with optical or acoustic readers. Biosensors can be configured to allow the data collected to be electronically transmitted to the physician for interpretation and thus can form the basis for e-neuromedicine.

Any suitable animal may be used as a subject non-human animal, for example a non-human primate, horse, cow, pig, goat, sheep, dog, cat, fish, rodent, e.g. guinea pig, rat or mouse; insect (e.g. *Drosophila*), amphibian (e.g. *Xenopus*) or *C. elegans*.

There is provided a method of identifying a substance capable of promoting or suppressing the generation of the biomarker in a subject, comprising exposing a test cell to a test substance and monitoring the level of the biomarker within said test cell, or secreted by said test cell.

The test cell could be prokaryotic, however a eukaryotic cell will suitably be employed in cell-based testing methods. Suitably, the eukaryotic cell is a yeast cell, insect cell, *Drosophila* cell, amphibian cell (e.g. from *Xenopus*), *C. elegans* cell or is a cell of human, non-human primate, equine, bovine, porcine, caprine, ovine, canine, feline, piscine, rodent or murine origin.

The test substance can be a known chemical or pharmaceutical substance, such as, but not limited to, an antipsychotic disorder therapeutic; or the test substance can be novel synthetic or natural chemical entity, or a combination of two or more of the aforesaid substances.

In methods for identifying substances of potential therapeutic use, non-human animals or cells can be used that are capable of expressing the biomarker.

Screening methods also encompass a method of identifying a ligand capable of binding to the biomarker according to the invention, comprising incubating a test substance in the presence of the biomarker in conditions appropriate for binding, and detecting and/or quantifying binding of the biomarker to said test substance.

High-throughput screening technologies based on the biomarker, uses and methods of the invention, e.g. configured in an array format, are suitable to monitor biomarker signatures for the identification of potentially useful therapeutic compounds, e.g. ligands such as natural compounds, synthetic chemical compounds (e.g. from combinatorial libraries), peptides, monoclonal or polyclonal antibodies or fragments thereof, which may be capable of binding the biomarker.

Methods of the invention can be performed in array format, e.g. on a chip, or as a multiwell array. Methods can be adapted into platforms for single tests, or multiple identical or multiple non-identical tests, and can be performed in high throughput format. Methods of the invention may comprise performing one or more additional, different tests to confirm or exclude diagnosis, and/or to further characterise a condition.

The invention further provides a substance, e.g. a ligand, identified or identifiable by an identification or screening method or use of the invention. Such substances may be capable of inhibiting, directly or indirectly, the activity of the biomarker, or of suppressing generation of the biomarker. The term "substances" includes substances that do not directly bind the biomarker and directly modulate a function, but instead indirectly modulate a function of the biomarker. Ligands are also included in the term substances; ligands of the invention (e.g. a natural or synthetic chemical compound, peptide, aptamer, oligonucleotide, antibody or antibody fragment) are capable of binding, suitably specific binding, to the biomarker.

The invention further provides a substance according to the invention for use in the treatment of bipolar disorder, or predisposition thereto.

In one embodiment, the method additionally comprises administering a bipolar disorder medicament to a patient who is diagnosed with or predicted to have bipolar disorder.

Thus, according to a further aspect of the invention there is provided a method of treating a bipolar disorder patient, which comprises the step of administering a bipolar disorder medicament to a patient identified as having differing levels of the biomarkers as defined herein when compared to the levels of said biomarkers from a normal subject.

According to a further aspect of the invention there is provided a method of treating a bipolar disorder patient, which comprises the following steps:
(a) quantifying the amounts of the biomarkers as defined herein in a biological sample obtained from an individual;
(b) comparing the amounts of the biomarkers in the biological sample with the amounts present in a normal control biological sample from a normal subject, such that a difference in the level of the biomarkers in the biological sample is indicative of bipolar disorder, or predisposition thereto; and
(c) administering a bipolar disorder medicament to a patient diagnosed in step (b) as a patient with bipolar disorder.

Also provided is the use of a substance according to the invention in the treatment of bipolar disorder, or predisposition thereto.

Also provided is the use of a substance according to the invention as a medicament.

Diagnostic Kits

A further aspect of the invention provides a kit for diagnosing and/or monitoring bipolar disorder comprising reagents and/or a biosensor capable of detecting and/or quantifying the biomarkers described herein. Suitably a kit according to the invention may contain one or more components selected from the group: a ligand specific for the biomarker or a structural/shape mimic of the biomarker, one or more controls, one or more reagents and one or more consumables; optionally together with instructions for use of the kit in accordance with any of the methods defined herein.

In one embodiment, the kit additionally comprises a questionnaire for use in diagnosing a patient with bipolar disorder. The questionnaire may be used to support the results obtained from use of the kit and/or to help determine the severity of bipolar disorder (i.e. severe, moderate or mild). In a further embodiment, the questionnaire is the Hamilton Rating scale for depression (HAM-D, 17, 21 or 29 items) questionnaire. Other examples of suitable questionnaires which may be used, include: the Montgomery-Asberg Depression Rating Scale (MADRS), the Beck Depression Inventory (BDI), the Zung Self-Rating Depression Scale, the Wechsler Depression Rating Scale, the Raskin Depression Rating Scale, the Inventory of Depressive Symptomatology (IDS) or the Quick Inventory of Depressive Symptomatology (QIDS).

Diagnostic kits for the diagnosis and monitoring of bipolar disorder are described herein. In one embodiment, the kits additionally contain a biosensor capable of detecting and/or quantifying a biomarker.

The identification of biomarkers for bipolar disorder permits integration of diagnostic procedures and therapeutic regimes. Currently there are significant delays in determining effective treatment and hitherto it has not been possible to perform rapid assessment of drug response. Traditionally, many anti-depressive or anti-psychotic therapies have required treatment trials lasting weeks to months for a given therapeutic approach. Detection of a biomarker of the invention can be used to screen subjects prior to their participation in clinical trials. The biomarkers provide the means to indicate therapeutic response, failure to respond, unfavourable side-effect profile, degree of medication compliance and achievement of adequate serum drug levels. The biomarkers may be used to provide warning of adverse drug response. Biomarkers are useful in development of personalized brain therapies, as assessment of response can be used to fine-tune dosage, minimise the number of prescribed medications, reduce the delay in attaining effective therapy and avoid adverse drug reactions. Thus by monitoring a biomarker of the invention, patient care can be tailored precisely to match the needs determined by the disorder and the pharmacogenomic profile of the patient, the biomarker can thus be used to titrate the optimal dose, predict a positive therapeutic response and identify those patients at high risk of severe side effects.

Biomarker-based tests provide a first line assessment of 'new' patients, and provide objective measures for accurate and rapid diagnosis, in a time frame and with precision, not achievable using the current subjective measures.

Furthermore, diagnostic biomarker tests are useful to identify family members or patients at high risk of developing bipolar disorder. This permits initiation of appropriate therapy, or preventive measures, e.g. managing risk factors. These approaches are recognised to improve outcome and may prevent overt onset of the disorder.

Biomarker monitoring methods, biosensors and kits are also vital as patient monitoring tools, to enable the physician to determine whether relapse is due to worsening of the disorder, poor patient compliance or substance abuse. If pharmacological treatment is assessed to be inadequate, then therapy can be reinstated or increased; a change in therapy can be given if appropriate. As the biomarker is sensitive to the state of the disorder, it provides an indication of the impact of drug therapy or of substance abuse.

Reference Standards for Treatment

In many embodiments, the levels of one or more biomarkers or the levels of a specific panel of biomarkers in a sample are compared to a reference standard ("reference standard" or "reference level") in order to direct treatment decisions. The reference standard used for any embodiment disclosed herein may comprise average, mean, or median levels of the one or more biomarkers or the levels of the specific panel of biomarkers in a control population. The reference standard may additionally comprise cutoff values or any other statistical attribute of the control population, such as a standard deviation from the mean levels of the one or more biomarkers or the levels of the specific panel of biomarkers.

In some embodiments, comparing the level of the one or more biomarkers is performed using a cutoff value. In related embodiments, if the level of the one or more biomarkers is greater than the cutoff value, the individual may be diagnosed as having, or being at risk of developing bipolar disorder. In other distinct embodiments, if the level of the one or more biomarkers is less than the cutoff value, the individual may be diagnosed as having, or being at risk of developing bipolar disorder. Cutoff values may be determined by statistical analysis of the control population to determine which levels represent a high likelihood that an individual does or does not belong to the control population. In some embodiments, comparing the level of the one or more biomarkers is performed using other statistical methods. In related embodiments, comparing comprises logistic or linear regression. In other embodiments, comparing comprises computing an odds ratio.

In some embodiments, the control population may comprise healthy individuals or individuals with bipolar disorder.

In some embodiments, individuals with levels of one or more biomarkers or levels of a specific panel of biomarkers greater than the reference levels would be more likely to have bipolar disorder. Therefore, an individual presenting with levels of the one or more biomarkers or levels of the specific panel of biomarkers greater than the reference standard would be a candidate for treatment with antidepressant or anxiolytic therapy, or with more aggressive therapy. On the other hand, an individual presenting with levels of the one or more biomarkers or levels of the specific panel of biomarkers less than or equal to the reference standard would be less likely to have bipolar disorder and therefore be a candidate for no antidepressant or anxiolytic therapy, delayed antidepressant or anxiolytic therapy or less aggressive antidepressant or anxiolytic therapy.

In other embodiments, individuals with levels of one or more biomarkers or levels of a specific panel of biomarkers less than the reference levels would be more likely to have bipolar disorder. Therefore, an individual presenting with levels of the one or more biomarkers or levels of the specific panel of biomarkers less than the reference standard would be a candidate for treatment with antidepressant or anxiolytic therapy, or with more aggressive therapy. On the other hand, an individual presenting with levels of the one or more biomarkers or levels of the specific panel of biomarkers greater than or equal to the reference standard would be less likely to have bipolar disorder and therefore be a candidate for no antidepressant or anxiolytic therapy, delayed antidepressant or anxiolytic therapy or less aggressive antidepressant or anxiolytic therapy.

Reference Therapy for Treatment

In some embodiments, a patient is treated more or less aggressively than a reference therapy. A reference therapy is any therapy that is the standard of care for bipolar disorder. The standard of care can vary temporally and geographically, and a skilled person can easily determine the appropriate standard of care by consulting the relevant medical literature.

In some embodiments, based on a determination that levels of a panel of biomarkers is a) greater than, b) less than, c) equal to, d) greater than or equal to, or e) less than or equal to a reference standard, treatment will be either 1) more aggressive, or 2) less aggressive than a standard therapy.

In some embodiments, a more aggressive therapy than the standard therapy comprises beginning treatment earlier than in the standard therapy. In some embodiments, a more aggressive therapy than the standard therapy comprises administering additional treatments than in the standard therapy. In some embodiments, a more aggressive therapy than the standard therapy comprises treating on an accelerated schedule compared to the standard therapy. In some embodiments, a more aggressive therapy than the standard therapy comprises administering additional treatments not called for in the standard therapy.

In some embodiments, a less aggressive therapy than the standard therapy comprises delaying treatment relative to the standard therapy. In some embodiments, a less aggressive therapy than the standard therapy comprises administering less treatment than in the standard therapy. In some embodiments, a less aggressive therapy than the standard therapy comprises administering treatment on a decelerated schedule compared to the standard therapy. In some embodiments, a less aggressive therapy than the standard therapy comprises administering no treatment.

Treatment of Depression

Health practitioners treat depression by taking actions to ameliorate the causes or symptoms of the disorder in a patient. Treatment may comprise drug-based or non-drug-based therapies.

Drug-based therapies may include: selecting and administering one or more antidepressant drugs to the patient, adjusting the dosage of an antidepressant drug, adjusting the dosing schedule of an antidepressant drug, and adjusting the length of the therapy with an antidepressant drug. Antidepressant drugs are selected by practitioners based on the nature of the symptoms and the patient's response to any previous treatments. The dosage of an antidepressant drug can be adjusted as well by the practitioner based on the nature of the drug, the nature of the patient's symptoms, the patient's response to previous treatment, and the patient's response to the drug. The dosing schedule can also be adjusted by the practitioner based on the nature of the drug, the nature of the patient's symptoms, the patient's response to previous treatment, and the patient's response to the drug. Also, the length of the therapy can be adjusted by the practitioner based on the nature of the drug, the nature of the patient's symptoms, the patient's response to previous treatment, and the patient's response to the drug. Additionally, the practitioner can select between a single drug therapy, a dual drug therapy, or a triple drug therapy. In some embodiments, a practitioner may optionally treat the patient with a combination of one or more antidepressant drugs and one or more non-drug-based therapies. In one embodiment, the practitioner begins antidepressant therapy based on a comparison between a reference level and the levels of one or more biomarkers or the levels of a specific panel of biomarkers in a sample from a patient. In one embodiment, therapy comprises the selection and administration of an antidepressant drug to the patient by the practitioner. In another embodiment, therapy comprises the selection and administration of two antidepressant drugs to the patient by the practitioner as part of dual therapy. In another embodiment, therapy comprises the selection and administration of three antidepressant drugs to the patient by the practitioner as part of triple therapy.

Antidepressant drugs are commonly used by medical practitioners, and a skilled person may identify the appropriate antidepressant drug to administer based on the medical literature. In some embodiments, treatment comprises administering to an individual a selective serotonin reuptake inhibitor ("SSRI"). In some embodiments, the SSRI is citalopram. In some embodiments, the SSRI is escitalopram. In some embodiments, the SSRI is fluoxetine. In some embodiments, the SSRI is paroxetine. In some embodiments, the SSRI is sertraline.

In other embodiments, treatment comprises administering to an individual a serotonin-norepinephrine reuptake inhibitors ("SNRI"). In some embodiments, the SNRI is venlafaxine. In other embodiments, the SNRI is duloxetine.

In other embodiments, treatment comprises administering to an individual a norepinephrine and dopamine reuptake inhibitor ("NDRI"). In one embodiment, the NDRI is bupropion.

In other embodiments, treatment comprises administering to an individual a tetracyclic antidepressant ("tetracyclic"). In some embodiments, the tetracyclic is amoxapine. In some embodiments, the tetracyclic is maprotiline. In some embodiments, the tetracyclic is mazindol. In some embodiments, the tetracyclic is mirtazapine.

In other embodiments, treatment comprises administering to an individual a tricyclic antidepressant ("tricyclic"). In some embodiments, the tricyclic is amitriptyline. In some embodiments, the tricyclic is imipramine. In some embodiments, the tricyclic is nortriptyline.

In other embodiments, treatment comprises administering to an individual a monoamine oxidase inhibitor ("MAOI"). In some embodiments, the MAOI is selegiline. In some embodiments, the MAOI is isocarboxazid. In some embodiments, the MAOI is phenelzine. In some embodiments, the MAOI is tranylcypromine.

In addition to or in lieu of drug-based therapies, in some embodiments a practitioner may also treat an individual with non-drug-based antidepressant therapies. In some embodiments, the non-drug based therapy comprises cognitive-behavioral therapy. In some embodiments, the non-drug based therapy comprises psychotherapy. In a related embodiment, the non-drug based therapy comprises psychodynamic therapy. In some embodiments, the non-drug based therapy comprises electroconvulsive therapy. In some embodiments, the non-drug based therapy comprises hospitalization and residential treatment programs. In some embodiments, the non-drug based therapy comprises vagus nerve stimulation. In some embodiments, the non-drug based therapy comprises transcranial magnetic stimulation. In some embodiments, the non-drug based therapy comprises regular, vigorous exercise.

In one embodiment, the practitioner adjusts the antidepressant therapy based on a comparison between a reference level and the levels of one or more biomarkers or the levels of a specific panel of biomarkers in a sample from a patient.

In one embodiment, the practitioner adjusts the therapy by selecting and administering a different drug. In one embodiment, the practitioner adjusts the therapy by selecting and administering a different combination of drugs. In one embodiment, the practitioner adjusts the therapy by adjusting drug dosage. In one embodiment, the practitioner adjusts the therapy by adjusting dose schedule. In one embodiment, the practitioner adjusts the therapy by adjusting length of therapy. In one embodiment, the practitioner adjusts the therapy by selecting and administering a different drug combination and adjusting drug dosage. In one embodiment, the practitioner adjusts the therapy by selecting and administering a different drug combination and adjusting dose schedule. In one embodiment, the practitioner adjusts the therapy by selecting and administering a different drug combination and adjusting length of therapy. In one embodiment, the practitioner adjusts the therapy by adjusting drug dosage and dose schedule. In one embodiment, the practitioner adjusts the therapy by adjusting drug dosage and adjusting length of therapy. In one embodiment, the practitioner adjusts the therapy by adjusting dose schedule and adjusting length of therapy. In one embodiment, the practitioner adjusts the therapy by selecting and administering a different drug, adjusting drug dosage, and adjusting dose schedule. In one embodiment, the practitioner adjusts the therapy by selecting and administering a different drug, adjusting drug dosage, and adjusting length of therapy. In one embodiment, the practitioner adjusts the therapy by selecting and administering a different drug, adjusting dose schedule, and adjusting length of therapy. In one embodiment, the practitioner adjusts the therapy by adjusting drug dosage, adjusting dose schedule, and adjusting length of therapy. In one embodiment, the practitioner adjusts the therapy by selecting and administering a different drug, adjusting drug dosage, adjusting dose schedule, and adjusting length of therapy.

In some embodiments, treatment comprises a less aggressive therapy than a reference therapy. In one embodiment a less aggressive therapy comprises not administering drugs and taking a "watchful waiting" approach. In one embodiment a less aggressive therapy comprises delaying treatment. In one embodiment a less aggressive therapy comprises selecting and administering less potent drugs. In one embodiment a less aggressive therapy comprises decreasing dosage of antidepressant drugs. In one embodiment a less aggressive therapy comprises decreasing the frequency treatment. In one embodiment a less aggressive therapy comprises shortening length of therapy. In one embodiment, less aggressive therapy comprises selecting and administering less potent drugs and decreasing drug dosage. In one embodiment, less aggressive therapy comprises selecting and administering less potent drugs and decelerating dose schedule. In one embodiment, less aggressive therapy comprises selecting and administering less potent drugs and shortening length of therapy. In one embodiment, less aggressive therapy comprises decreasing drug dosage and decelerating dose schedule. In one embodiment, less aggressive therapy comprises decreasing drug dosage and shortening length of therapy. In one embodiment, less aggressive therapy comprises decelerating dose schedule and shortening length of therapy. In one embodiment, less aggressive therapy comprises selecting and administering less potent drugs, decreasing drug dosage, and decelerating dose schedule. In one embodiment, less aggressive therapy comprises selecting and administering less potent drugs, decreasing drug dosage, and shortening length of therapy. In one embodiment, less aggressive therapy comprises selecting and administering less potent drugs, decelerating dose schedule, and shortening length of therapy. In one embodiment, less aggressive therapy comprises decreasing drug dosage, decelerating dose schedule, and shortening length of therapy. In one embodiment, less aggressive therapy comprises selecting and administering less potent drugs, decreasing drug dosage, decelerating dose schedule, and shortening length of therapy. In some embodiments, a less aggressive therapy comprises administering only non-drug-based therapies.

In another aspect of the present application, treatment comprises a more aggressive therapy than a reference therapy. In one embodiment a more aggressive therapy comprises earlier administration of antidepressant drugs. In one embodiment a more aggressive therapy comprises increased dosage of antidepressant drugs. In one embodiment a more aggressive therapy comprises increased length of therapy. In one embodiment a more aggressive therapy comprises increased frequency of the dose schedule. In one embodiment, more aggressive therapy comprises selecting and administering more potent drugs and increasing drug dosage. In one embodiment, more aggressive therapy comprises selecting and administering more potent drugs and accelerating dose schedule. In one embodiment, more aggressive therapy comprises selecting and administering more potent drugs and increasing length of therapy. In one embodiment, more aggressive therapy comprises increasing drug dosage and accelerating dose schedule. In one embodiment, more aggressive therapy comprises increasing drug dosage and increasing length of therapy. In one embodiment, more aggressive therapy comprises accelerating dose schedule and increasing length of therapy. In one embodiment, more aggressive therapy comprises selecting and administering more potent drugs, increasing drug dosage, and accelerating dose schedule. In one embodiment, more aggressive therapy comprises selecting and administering more potent drugs, increasing drug dosage, and increasing length of therapy. In one embodiment, more aggressive therapy comprises selecting and administering more potent drugs, accelerating dose schedule, and increasing length of therapy. In one embodiment, more aggressive therapy comprises increasing drug dosage, accelerating dose schedule, and increasing length of therapy. In one embodiment, more aggressive therapy comprises selecting and administering more potent drugs, increasing drug dosage, accelerating dose schedule, and increasing length of therapy. In some embodiments, a more aggressive therapy comprises administering a combination of drug-based and non-drug-based therapies.

Systems for Diagnosing and Treating Depression

The results of any analyses according to the invention will often be communicated to physicians and/or patients (or other interested parties such as researchers) in a transmittable form that can be communicated or transmitted to any of the above parties. Such a form can vary and can be tangible or intangible. The results can be embodied in descriptive statements, diagrams, photographs, charts, images or any other visual forms. The statements and visual forms can be recorded on a tangible medium such as papers, computer readable media such as hard disks, compact disks, etc., or on an intangible medium, e.g., an electronic medium in the form of email or website on internet or intranet. In addition, results can also be recorded in a sound form and transmitted through any suitable medium, e.g., analog or digital cable lines, fiber optic cables, etc., via telephone, facsimile, wireless mobile phone, internet phone and the like.

Thus, the information and data on a test result can be produced anywhere in the world and transmitted to a different location. As an illustrative example, when an assay is conducted outside the United States, the information and data on a test result may be generated, cast in a transmittable form as described above, and then imported into the United States. Accordingly, the present invention also encompasses a method for producing a transmittable form of information on levels of one or more biomarkers or levels of a specific panel of biomarkers for at least one patient sample. The method comprises the steps of (1) determining levels of one or more biomarkers or levels of a specific panel of biomarkers for at least one patient sample according to methods of the present invention; and (2) embodying the result of the determining step in a transmittable form. The transmittable form is the product of such a method.

Techniques for analyzing levels of one or more biomarkers or levels of a specific panel of biomarkers for at least one patient sample will often be implemented using hardware, software or a combination thereof in one or more computer systems or other processing systems capable of effectuating such analysis.

Thus, the present invention further provides a system for determining whether an individual suffers from bipolar disorder, comprising: (1) a sample analyzer for determining the levels of one or more biomarkers or levels of a specific panel of biomarkers for at least one patient sample, wherein the sample analyzer contains the patient sample; (2) a first computer program for (a) receiving data regarding the levels of one or more biomarkers or the levels of a specific panel of biomarkers; and optionally (3) a second computer program for comparing the test value to one or more reference standards each associated with a predetermined degree of risk of bipolar disorder.

The sample analyzer can be any instruments useful in determining the levels of biomarkers in a sample, as described herein.

The computer-based analysis function can be implemented in any suitable language and/or browsers. For example, it may be implemented with C language and preferably using object-oriented high-level programming languages such as Visual Basic, SmallTalk, C++, and the like. The application can be written to suit environments such as the Microsoft Windows™ environment including Windows™ 98, Windows™ 2000, Windows™ NT, and the like. In addition, the application can also be written for the MacIntosh™, SUN™, UNIX or LINUX environment. In addition, the functional steps can also be implemented using a universal or platform-independent programming language. Examples of such multi-platform programming languages include, but are not limited to, hypertext markup language (HTML), JAVA™, JavaScript™, Flash programming language, common gateway interface/structured query language (CGI/SQL), practical extraction report language (PERL), AppleScript™ and other system script languages, programming language/structured query language (PL/SQL), and the like. Java™- or JavaScript™-enabled browsers such as HotJava™, Microsoft™ Explorer™, or Netscape™ can be used. When active content web pages are used, they may include Java™ applets or ActiveX™ controls or other active content technologies.

The analysis function can also be embodied in computer program products and used in the systems described above or other computer- or internet-based systems. Accordingly, another aspect of the present invention relates to a computer program product comprising a computer-usable medium having computer-readable program codes or instructions embodied thereon for enabling a processor to carry out disease risk analysis. These computer program instructions may be loaded onto a computer or other programmable apparatus to produce a machine, such that the instructions which execute on the computer or other programmable apparatus create means for implementing the functions or steps described above. These computer program instructions may also be stored in a computer-readable memory or medium that can direct a computer or other programmable apparatus to function in a particular manner, such that the instructions stored in the computer-readable memory or medium produce an article of manufacture including instructions which implement the analysis. The computer program instructions may also be loaded onto a computer or other programmable apparatus to cause a series of operational steps to be performed on the computer or other programmable apparatus to produce a computer implemented process such that the instructions which execute on the computer or other programmable apparatus provide steps for implementing the functions or steps described above.

Thus one aspect of the present invention provides a system for determining whether a patient has bipolar disorder. Generally speaking, the system comprises (1) computer program for receiving, storing, and/or retrieving data regarding levels of biomarkers in a patient's sample and optionally clinical parameter data (e.g., disease-related symptoms); (2) computer program for querying this patient data; (3) computer program for concluding whether an individual suffers from bipolar disorder based on this patient data; and optionally (4) computer program for outputting/displaying this conclusion. In some embodiments this computer program for outputting the conclusion may comprise a computer program for informing a health care professional of the conclusion.

The practice of the present invention may also employ conventional biology methods, software and systems. Computer software products of the invention typically include computer readable media having computer-executable Instructions for performing the logic steps of the method of the invention. Suitable computer readable medium include floppy disk, CD-ROM/DVD/DVD-ROM, hard-disk drive, flash memory, ROM/RAM, magnetic tapes and etc. Basic computational biology methods are described in, for example, Setubal et al., INTRODUCTION TO COMPUTATIONAL BIOLOGY METHODS (PWS Publishing Company, Boston, 1997); Salzberg et al. (Ed.), COMPUTATIONAL METHODS IN MOLECULAR BIOLOGY, (Elsevier, Amsterdam, 1998); Rashidi & Buehler, BIOINFORMATICS BASICS: APPLICATION IN BIOLOGICAL SCIENCE AND MEDICINE (CRC Press, London, 2000); and Ouelette & Bzevanis, Page 38 of 64 BIOINFORMATICS: A PRACTICAL GUIDE FOR ANALYSIS OF GENE AND PROTEINS (Wiley & Sons, Inc., 2nd ed., 2001); see also, U.S. Pat. No. 6,420,108.

The following studies illustrate the invention.

Example 1: Identification of a Diagnostic Biomarker Panel for Bipolar Disorder

Methods

The present study consisted of discovery, validation and application stages. In the discovery stage, a mood-state-independent diagnostic biomarker panel was defined for BD in a meta-analysis of eight independent case-control studies from five different clinical centres. The eight studies included a total of 158 established BD patients and 143 controls. In the validation stage, it was attempted to validate the predictive performance of the diagnostic biomarker panel in a case-control study consisting of a further 66 established BD patients and 44 controls. Finally, in the application stage, the predictive performance of the diagnostic biomarker panel was applied and evaluated in undiagnosed BD patients and the disease specificity of the panel was tested. The diagnostically relevant patients included pre-symptomatic BD patients, first onset "MDD patients" including individuals who later developed BD, pre-symptomatic SCZ patients and drug-naïve, first-onset SCZ patients.

Study Participants

In the discovery stage, eight independent case-control studies were investigated in a meta-analysis. Patients were recruited in four clinical centres in Germany (Cologne, Magdeburg, Münster and Würzburg) and one in the Netherlands (Rotterdam). The recruitment inclusion and exclusion criteria were similar for all cohorts. The criteria required male and female participants to be within the age range of 18-60 years, have a body mass index (BMI) between 18 and 40 $kg/m^2$, and test negative for recreational drug screening at the time of sampling (see Table 1).

TABLE 1

Demographical summary of the eight case-control studies used in the meta-analysis (discovery stage), the validation stage and the application stage

| | | Cohort | | | | | | | |
|---|---|---|---|---|---|---|---|---|---|
| | | Rotterdam | | | | Würzburg | | | |
| | | Study | | | | | | | |
| | | 1 | | 2 | | 3 | | 4 | |
| | | Group | | | | | | | |
| | | C | BD | C | BD | C | BD | C | BD |
| | | Sample size | | | | | | | |
| Discovery stage | | 40 | 10 | 13 | 28 | 6 | 15 | 18 | 60 |
| | Age [SD] | 26.8 [4.1] | 28.3 [11.1] | 42.6 [12.3] | 47.3 [12.8] | 44.5 [15.9] | 46.4 [13.5] | 45.7 [10.4] | 47 [10.9] |
| | Sex (m/f) | 33/7 | 7/3 | 6/7 | 11/17 | 3/3 | 6/7 | 7/11 | 29/31 |
| | BD subtype (1/2) | / | NR | / | 15/13 | / | 5/10 | / | 30/30 |
| | Mood state (d/e/m/mixed/NO) | / | NR | / | 19/0/4/5/0 | / | 1/3/6/5/0 | / | 27/31/1/0 |
| | somatic medication | NA | NA | 5/13 | 14/28 | 0/6 | 11/15 | 4/18 | 37/60 |
| | psychiatric medication | 0/40 | 6/10 | 0/13 | 28/28 | 0/6 | 15/15 | 0/18 | 57/60 |
| | Mood stabilizer | 0/40 | NA | 0/13 | 11/28 | 0/6 | 7/15 | 0/18 | 55/60 |
| | Anti-depressant | 0/40 | 6/10 | 0/13 | 16/28 | 0/6 | 2/15 | 0/18 | 37/60 |
| | Antipsychiotic | NA | NA | 0/13 | 24/28 | 0/6 | 8/15 | 0/18 | 16/60 |
| | BMI [SD] | NA | NA | 26.0 [4.7]* | 27.5 [6.4]* | NA | NA | 23.6 [3.2]* | 27.8 [5.5]* |
| | Smoker | 10/40 | 10/10 | 4/13 | 11/28 | 1/6 | 4/15 | 2/18 | 21/60 |
| | Canabis life time | NA | 6/10 | NA | NA | NA | NA | NA | NA |
| | Molecular profiling | May 2009 | | November 2010 | | August 2011 | | June 2012 | |

TABLE 1-continued

Demographical summary of the eight case-control studies used in the meta-analysis (discovery stage), the validation stage and the application stage

| | | Cohort | | | | | | | |
|---|---|---|---|---|---|---|---|---|---|
| | | Magedeburg | | | | Study Cologne | | Münster | |
| | | 5 | | 6 | | 7 | | 8 | |
| | | | | | | Group Sample size | | | |
| | | C | BD | C | BD | C | BD | C | BD |
| | | 15 | 7 | 13 | 5 | 12 | 15 | 26 | 18 |
| Discovery stage | Age [SD] | 40.8 [7.7] | 40.4 [7.7] | 29.2 [5.8] | 28.8 [6.0] | 41.7 [7.6] | 44.1 [11.1] | 44.6 [9.5] | 47.3 [14.2] |
| | Sex (m/f) | 5/10 | 2/5 | 8/5 | 3/2 | 6/6 | 5/10 | 10/16 | 10/8 |
| | BD subtype (1/2) | / | NR | / | NR | / | NA | / | NR |
| | Mood state (d/e/m/mixed/NO) | / | NR | / | NR | / | NA | / | NR |
| | somatic medication | NR | NR | NR | NR | 4/12 | 2/15 | 0/26 | NR |
| | psychiatric medication | 0/15 | 0/7 | 0/13 | NR | 0/12 | 15/15 | 0/26 | NR |
| | Mood stabilizer | 0/15 | 0/7 | 0/13 | NR | 0/12 | 8/15 | 0/26 | NR |
| | Anti-depressant | 0/15 | 0/7 | 0/13 | NR | 0/12 | 3/15 | 0/26 | NR |
| | Antipsychiotic | 0/15 | 0/7 | 0/13 | NR | 0/12 | 2/15 | 0/26 | NR |
| | BMI [SD] | 25.5 [3.7] | 26.8 [7.2] | 23.3 [2.1] | 23.1 [3.3] | NA | NA | NR | NR |
| | Smoker | 9/15 | 5/7 | 3/13 | 1/5 | 2/15 | 11/15 | NR | NR |
| | Canabis life time | 1/15 | 1/7 | 0/13 | 0/5 | 1/12 | 2/15 | NR | NR |
| | Molecular profiling | September 2010 | | March 2011 | | March 2011 | | March 2011 | |

TABLE 1-continued

Demographical summary of the eight case-control studies used in the meta-analysis (discovery stage), the validation stage and the application stage

|  |  | Study Würzburg | | | Study | | | | | |
|---|---|---|---|---|---|---|---|---|---|---|
|  |  | | | | NESDA | | | USA Military | | Santander |
|  |  | Disease group | | | First depressive episode patients | | | Disease group | | |
|  |  | | | Application stage | First-onset | | | Pre-symptomatic | | First-onset, drug-naïve |
|  |  | Controls | BD | | MDD | Un-diagnosed BD | Controls | BD | SCZ | Controls | SCZ |
|  |  | Sample size | | | Sample size | | | Sample size | | | |
| Validation stage |  | 44 | 66 |  | 90 | 12 | 184 | 110 | 75 | 88 | 47 |
|  | Age [SD] | 29.2 [8.9] | 41.9 [13.4] | Age [SD] | 38.5 [13.4] | 35.4 [10.2] | 22.4 [3.6] | 21.3 [4.2] | 24.3 [4.5] | 33.1 [8.0] | 30.1 [9.0] |
|  | Sex (m/f) | 23/20 | 24/39 | Sex (m/f) | 33/57 | 5/7 | 136/48 | 70/40 | 67/8 | 51/37 | 28/19 |
|  | BD subtype (1/2/NOS) | / | 35/23/8 | BD subtype (1/2) | / | / | / | / | / | / | / |
|  | Mood state (d/e/m/mixed/NO) | / | 28/8/13/13/4 | Mood state (d/e/m/mixed) | / | 12/12 | / | / | / | / | / |
|  | somatic medication | 11/44 | 22/66 |  | 22/90 | 2/12 | NR | NR | NR | NR | NR |
|  | psychiatric medication | 0/44 | 45/66 |  | 39/90 | 2/12 | 0/184 | 0/184 | 0/184 | 0/184 | 0/184 |
|  | Mood stabilizer | 0/44 | 41/66 |  | 0/90 | 0/12 | 0/184 | 0/184 | 0/184 | 0/184 | 0/184 |
|  | Anti-depressant | 0/44 | 16/66 |  | 39/90 | 2/12 | 0/184 | 0/184 | 0/184 | 0/184 | 0/184 |
|  | Antipsychiotic | 0/44 | 23/66 |  | 39/90 | 0/12 | 0/184 | 0/184 | 0/184 | 0/184 | 0/184 |
|  | BMI [SD] | 23.8 [4.1]* | 27.6 [5.1]* |  | 25.6 [4.8] | 24.7 [2.7] | NR | NR | NR | 25.9 [3.8] | 23.3 [5.1] |
|  | Smoker | 10/44 | 23/66 |  | 31/90 | 8/12 | NR | NR | NR | NR | NR |
|  | Canabis life time | NA | NA |  | 3/90** | 1/12** | NR | NR | NR | 22/88 | 19/47 |
|  | Molecular profiling | Dez. 2013 | |  | April 2013 | | | June 2009 | | October 2013 | |

Analyte data was aquired between August 2005 and December 2013 (7 yrs 4 months).
NOS—Not other specified,
NR—Not recorded,
NA—information not available,
/ - not applicable,
*missing data points,
**cannabis in the past Month,
d—depressive,
e—euthymic,
m—manic,
NO—not other specified.

BD was diagnosed according to criteria of the International Classification of Diseases-10 (ICD-10) by a trained psychiatrist in a clinical setting using standard questionnaire based rating scales [Hamilton Depression Rating Scale (HAMD), Young Mania Rating Scale (YMRS) and Montgomery-Åsberg Depression Rating Scale (MADRS)]. Both bipolar I and bipolar II disorder patients were recruited. The BD patients were in one of the following mood states at the time of sample collection: depressed, mixed affective, hypomanic, manic or euthymic. Age and gender matched controls from similar geographical areas, with a similar socioeconomic background were recruited with a maximum delay of four weeks. The exclusion criteria included a diagnosis of coronary heart disease or cardiac insufficiency, autoimmune disorders, infections or treatment with immunosuppressive or immunomodulating drugs or antibiotics, other neuropsychiatric disorders or chronic terminal diseases affecting the brain, such as cancer or hepatic and renal insufficiency, alcohol or drug addiction. Patients and controls were fasting for at least two hours prior to blood sample collection. The study procedures and protocols received approval from the respective local ethical committees and informed written consent was obtained from all participants.

In the validation stage, the predictive performance of the diagnostic biomarker panel identified in the discovery stage was tested in a further case-control study from Würzburg in Germany (see Table 1). Clinical assessments, exclusion and inclusion criteria were as described for the discovery cohorts.

In the application stage, the predictive performance of the diagnostic biomarker panel was evaluated in three nested case-control studies drawn from the USA Military and NESDA, and in a case-control study from Santander (Spain). Two nested case-control studies were selected from the US Department of Defense Serum Repository (DoDSR), which contains over 55 million serum specimens remaining from mandatory HIV test samples of military personnel. Data and sera retrieval was performed by the Armed Forces Health Surveillance Center (AFHSC) and coordinated by the Military New-Onset Psychosis Project (MNOPP) investigators at the Walter Reed Army Institute of Research (WRAIR). The medical and demographic data were provided by the Defense Medical Surveillance System (DMSS), AFHSC, US DoD, Silver Spring, Md. [data range from 1971 to 2006; released in 2007] and serum specimens were retrieved from the DoDSR, AFHSC, US DoD (Silver Spring, Md., USA) [specimens range from 1988 to 2006, released in 2007]. Sera were then transferred to the Johns Hopkins School of Medicine (Baltimore, Md., USA) prior to testing. Samples were then selected from 185 individuals, who presented with psychiatric symptoms within 30 days after the blood collection and who received a DSM-IV diagnosis of either BD (296.00-296.06, 296.40-296.7, 296.80, 296.89) or SCZ (295.10-295.30, 295.60, 295.70, 295.90) (MNOPP) (Table 2)[21,22].

TABLE 2

A summary of the biomarkers forming the diagnostic biomarker panel and biomarker availability in the validation and application stages

| Biomarker panel | Validation stage | Discovery stage Application stage | | |
|---|---|---|---|---|
| | Würzburg | NESDA | USA Military | Santander |
| Angiotensin-Converting Enzyme (ACE) | ✓ | ✓ | ✓ | ✓ |
| Apolipoprotein A1 | ✓ | ✓ | ✓ | ✓ |
| CD40 Ligand | ✓ | ✓ | ✓ | ✓ |
| Carcinoembryonic Antigen (CEA) | Not measured | ✓ | ✓ | Not measured |
| EN-RAGE | ✓ | ✓ | ✓ | ✓ |
| Growth-Regulated alpha protein | Not measured | ✓ | ✓ | Not measured |
| Hepatocyte Growth Factor | ✓ | ✓ | ✓ | ✓ |
| Interleukin-10 | >20% missing | >20% missing | >20% missing | >20% missing |
| Interleukin-1 receptor antagonist | >20% missing | ✓ | ✓ | ✓ |
| Lipoprotein (a) | ✓ | ✓ | ✓ | ✓ |
| Macrophage Inflammatory Protein-1 beta (MIP-1 beta) | ✓ | ✓ | ✓ | ✓ |
| Matrix Metalloproteinase-3 | ✓ | ✓ | ✓ | ✓ |
| Serum Amyloid P-Component | ✓ | ✓ | ✓ | ✓ |
| Receptor for advanced glycosylation end products (RAGE) | ✓ | ✓ | ✓ | ✓ |
| Tumor Necrosis Factor Receptor-Like 2 | ✓ | ✓ | ✓ | ✓ |
| Apolipoprotein A2 | ✓ | ✓ | ✓ | ✓ |
| CD5 | ✓ | ✓ | ✓ | ✓ |
| Cystatin C | ✓ | ✓ | ✓ | ✓ |
| Matrix Metalloproteinase-7 | ✓ | ✓ | ✓ | ✓ |
| Matrix Metalloproteinase-9, total | ✓ | ✓ | ✓ | ✓ |
| | 20 | 16 | 18 | 19 | 17 |

Control subjects were selected from active duty military service population with no inpatient or outpatient psychiatric disorder diagnoses. All data were previously collected for other purposes, and analyses were conducted on de-identified data. An informed consent waiver was granted by the Institutional Review Board as only de-identified data were utilized.

The Netherlands Study of Depression and Anxiety (NESDA) is an eight-year longitudinal cohort study including 2,981 participants aged 18 through 65 years[23]. Patients from the NESDA were recruited from the general Dutch population, in general medical practices and in mental health organizations in order to recruit persons reflecting various settings and developmental stages of psychopathology. A four-hour baseline assessment including written questionnaires, interviews, a medical examination, a cognitive computer task and collection of blood and saliva samples, extensive information was gathered about key (mental) health outcomes and demographic, psychosocial, clinical, biological and genetic determinants. Detailed assessments were repeated after one, two, four and eight years of follow-up. Patients were recruited from three clinical sites in the Netherlands (Amsterdam, Groningen and Leiden)[23]. Serum from a subset of 1,701 participants was profiled. This subset included 102 recent onset MDD patients, 12 of which were diagnosed as having BD within two years of the baseline interview (see Table 1).

The case-control study from Santander[24], included first-onset and antipsychotic-naïve or unmedicated SCZ patients and matched controls. Diagnosis was performed according to DSM-IV categories by psychiatrists and additional analysis included Positive and Negative Syndrome Scale (PANSS) testing. Information on antipsychotic medication use was confirmed by direct contact with the treating family physicians, relatives and spouses along with consultations regarding detailed history of psychotropic medication use prior to hospitalization. Controls were recruited simultaneously from the community through advertisements or selected from a clinical database of volunteers (students, staff, relatives of staff, and blood donors from local blood banks) and matched with the respective patient groups for age, gender and other patient characteristics such as BMI, smoking and *cannabis* use, when this information was available. Those having first-degree relatives with a history of mental disease or other medical conditions such as type 2 diabetes mellitus, cardiovascular or autoimmune diseases, were not included in the study. SCZ patients with these co-morbidities were also excluded. In all instances, medication was administered after completion of diagnostic evaluation as appropriate. In addition, informed and written consent was given by all participants and the study protocols, analysis of samples and test methods were approved by the local Institutional Ethics Review Boards and were in compliance with the Standards for Reporting of Diagnostic Accuracy.

Sample Preparation

A blood sample was taken within two days of the clinical assessment. Serum was collected from acutely ill fasting patients and controls using Vacutainer (Becton-Dickinson, Franklin Lakes, N.J., USA). Blood clotting time was two hours at room temperature prior to centrifugation for 15 minutes at 1.100×g (respectively 5 minutes at 4000×g for study 1 and 5-8). Samples were stored in low binding Eppendorf tubes (Hamburg, Germany) at −80° C. Sample shipment took place on dry ice.

Multiplex Immunoassay Analysis

Serum from all participants was profiled using the multiplex immunoassay platform at Myriad Rules Based Medicine (Myriad RBM; Austin, Tex., USA). The Human DiscoveryMAP™ was used to measure the plasma concentrations of different proteins, peptides and small molecules (collectively referred to as 'analytes') in a Clinical Laboratory Improved Amendments certified lab. The number of analytes measured differed between the studies depending on when the study samples were profiled (total range: 147 to 257 analytes). The platform has been described previously[25].

Statistical Analysis

All statistical analyses were performed in R[26]. The analyte data from each study was pre-processed to exclude analytes with greater than 20% missing values and sample outliers were identified using the first two principal components[27], and to impute missing data (as described previously[28]; see Table 3). The data was $\log_{10}$-transformed to stabilize the variance.

TABLE 3

Summary of patients, controls and the analytes measured for each study

| Centre | Study | Before pre-processing | | | After pre-processing | | |
|---|---|---|---|---|---|---|---|
| | | Patients | Controls | Analytes | Patients | Controls | Analytes |
| Rotterdam | 1 | 10 | 40 | 181 | 10 | 40 | 133 |
| Würzburg | 2 | 28 | 13 | 190 | 28 | 13 | 129 |
| | 3 | 15 | 6 | 187 | 15 | 6 | 138 |
| | 4 | 60 | 18 | 257 | 60 | 18 | 173 |
| Magedeburg | 5 | 7 | 15 | 190 | 7 | 15 | 145 |
| | 6 | 5 | 13 | 188 | 5 | 13 | 138 |
| Cologne | 7 | 15 | 12 | 188 | 15 | 12 | 144 |
| Münster | 8 | 18 | 26 | 188 | 18 | 26 | 143 |
| Würzburg | Validation | 67 | 44 | 224 | 66 | 44 | 169 |
| NESDA | Application | 12 BD 90 MDD | 368-- | 243 | 12 BD 90 MDD | — | 167 |
| USA Military | Application | 110 BD 75 SCZ | 184 | 234 | 110 BD 75 SCZ | 184 | 178 |
| Santander | Application | 47 | 88 | 225 | 47 | 88 | 177 |

For the eight studies combined in the meta-analysis, ComBat[29] was used to adjust for the effects caused by running the study samples at different times (i.e. to make the subjects within and between the studies comparable). In addition, Combat was used to adjust the validation and application studies for batch effects caused by running samples within a study on different plates. ComBat is an empirical Bayes method of adjusting for additive, multiplicative, and exponential batch effects developed for analysing microarray data[29]. Combat was used as implemented in the sva package[30] in R.

After the pre-processing of the eight case-control studies, there were 115 analytes and two covariates (age and sex) in common across the studies (see Table 2). Before combining the studies in a meta-analysis, 28 analytes with significant BD association heterogeneity across the studies were excluded. The 87 remaining analytes and two covariates form $2^{89}$=6.2×$10^{26}$ possible candidate models. The model space was searched using lasso regression as implemented in the R package glmnet[31]. Lasso is a penalized method for restricting the residual sum of squares (deviance) and constraining the sum of the absolute values of the coefficients: $\Sigma_i |\beta| \leq t$, where t is the 'tuning' parameter. As t→∞, t has no effect and the solutions are the least squares estimates for the full model. For smaller t values, solutions are shrunken versions of the least squares estimates with many coefficients decreased to the null value. t was defined using ten-fold cross-validation[32], as the value of t minimizing the t-penalized residual sum of squares, which is equivalent to maximizing the t-penalized log likelihood. Although the coefficient estimates are biased to be small, a lasso estimator can have smaller error than a standard maximum likelihood estimator when applied to new data.

As the analytes were selected based on minimizing the t-penalized residual sum of squares, p-values for each of the selected analytes are not relevant and not reported. The predictive performance of the diagnostic biomarker panel was measured for sensitivity and specificity and area under the receiver operating characteristic (ROC) curves (AUC: 0.9-1=excellent; 0.8-0.9=good; 0.7-0.8=fair; 0.6-0.7=poor; 0.5-0.6=fail). Optimal trade-offs between sensitivity and specificity were determined by maximising Youden's index (J; where J=sensitivity+specificity−1).

It was attempted to validate the diagnostic biomarker panel in the independent case-control study from Würzburg (see Table 3). A logistic regression model was fit to the analyte data corresponding to the biomarker panel and predicted BD status. A similar approach was also adopted in the application stage. To test the predictive performance of the biomarker panel in pre-symptomatic SCZ and in drug-naïve, first onset SCZ patients, a fitted model derived from a BD patients and controls study was applied that was profiled and pre-processed at the same time as the SCZ study. For example, in the analysis of the USA Military studies, the logistic model was fitted to the pre-symptomatic BD patients and control data, and applied the fitted model to the pre-symptomatic SCZ patient and control data. As the studies were profiled at different times, not all of the analytes forming the diagnostic biomarker panel were available in the validation and application studies; some analytes were discontinued as Human DiscoveryMAP™ was developed and others failed at the pre-processing stage (e.g. greater than 20% missing values).

Results

Discovery Stage

Figure 1:
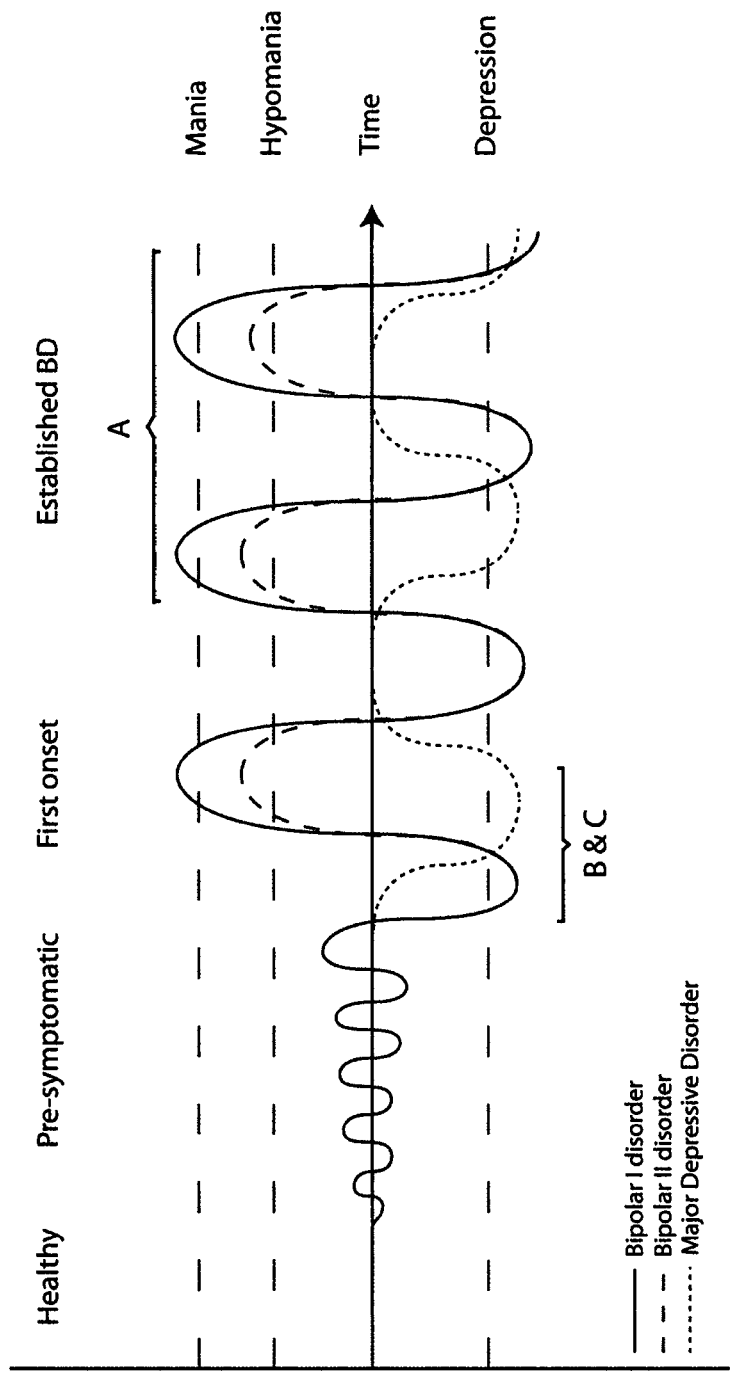
FIG. 1: A summary of the typical disease progression of BD and ROC curves derived from the discovery, validation and application stages. Middle section: typical course of BD starting from no overt symptoms, an initial depressive episode and followed by a chronic remitting-relapsing disease course is depicted by solid and dashed lines (BD I and BD II, respectively); the dotted line depicts a chronic MDD disease course. ROC curves and predictive performance: A) The discovery and validation stages—establised BD patients and controls; B) First onset "MDD patients" including individuals who later developed BD (NESDA); C) First onset MDD patients and controls (NESDA); D) Pre-symptomatic BD, pre-symptomatic SCZ and controls (USA military); E) Pre-symptomatic BD and pre-symptomatic SCZ (USA Military); and, F) first onset, drug-naïve SCZ patients and controls (Santander).
Figure 1A:
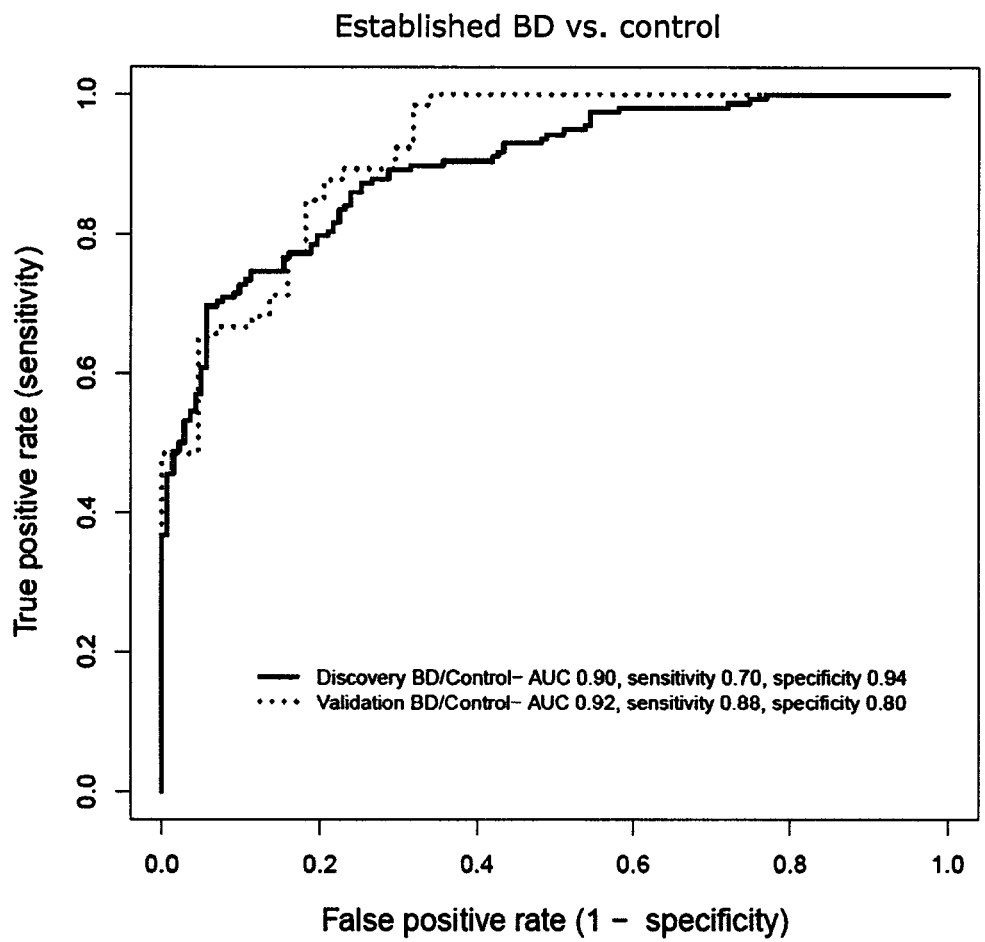

Eighty-seven analytes and two covariates (age and sex) were available across the eight case-control studies (183 BD patients and 149 controls) and included in the variable selection analysis to define the diagnostic biomarker panel. A biomarker panel of 20 analytes was identified with an excellent predictive performance (AUC=0.90; FIG. 1A) using lasso regression and cross-validation. Neither sex nor age were selected. When the selected analytes were grouped into functional pathways according to their molecular function in the peripheral system (Table 4), 11 analytes [CD40 Ligand, Macrophage Inflammatory Protein-1 beta, Serum Amyloid P-Component, EN-RAGE, Receptor for advanced glycosylation end products (RAGE), Tumor Necrosis Factor Receptor-Like 2, Growth-Regulated alpha protein, Interleukin-10, CD5, Interleukin-1 receptor antagonist and Carcinoembyonic antigen] were found to play a role in the inflammatory cascade. The majority of these analytes (7 out of 11) have a pro-inflammatory function and the remainder an anti-inflammatory role (Interleukin 10, CD5, Interleukin-1 receptor antagonist and Carcinoembyonic antigen). Another group of seven analytes can be clustered into lipid transport-related proteins (Apolipoprotein A1, Apolipoprotein A2 and Lipoprotein A) and proteins with metalloendopeptidase activity [Matrix Metalloproteinase-3, Matrix Metalloproteinase-7, Matrix Metalloproteinase-9 (total) and Angiotensin-Converting Enzyme]. Cystatin C (cysteine protease inhibitor) and Hepatocyte Growth factor do not cluster in one of the functional networks (Table 4).

TABLE 4

The 20 analytes selected in the discovery stage to form the diagnostic biomarker panel

| Molecular function | Analyte | Lasso-coefficient |
|---|---|---|
| Pro-inflammatory | CD40 Ligand | −0.11 |
| | EN-RAGE | 0.06 |
| | Growth-Regulated alpha protein | −1.81 |
| | Macrophage Inflammatory Protein-1 beta (MIP-1 beta) | 0.35 |
| | Receptor for advanced glycosylation end products (RAGE) | −0.30 |
| | Serum Amyloid P-Component | 1.41 |
| | Tumor Necrosis Factor Receptor-Like 2 | 3.43 |
| Anti-inflammatory | Carcinoembryonic Antigen (CEA) | 0.46 |
| | CD5 | −1.69 |
| | Interleukin-1 receptor antagonist | 0.36 |
| | Interleukin-10 | 0.78 |
| Lipid transport | Apolipoprotein A1 | −1.35 |
| | Apolipoprotein A2 | −0.37 |
| | Lipoprotein (a) | 0.20 |
| Metalloendopeptidase activity | Angiotensin-Converting Enzyme (ACE) | −0.49 |
| | Matrix Metalloproteinase-3 | −1.87 |
| | Matrix Metalloproteinase-7 | 2.50 |
| | Matrix Metalloproteinase-9, total | 0.33 |
| Cysteine protease inhibitor | Cystatin C | 0.53 |
| Growth factor | Hepatocyte Growth Factor | 0.23 |

Validation Stage

The diagnostic performance of the biomarker panel was tested in an independent case-control study from Würzburg consisting of a further 66 BD patients and 44 controls (see Table 1). Importantly, as in the meta-analysis, this study consisted of established BD patients in different mood states. The predictive performance of the biomarker panel was excellent (AUC=0.92; FIG. 1A) despite the panel being limited to 16 of the 20 analytes selected in the discovery stage (see Table 2). Note that the model fitted to the Würzburg study data, that is, the coefficients were estimated based upon the Würzburg study data and not upon the meta-analysis studies.

Application Stage

Figure 1B:
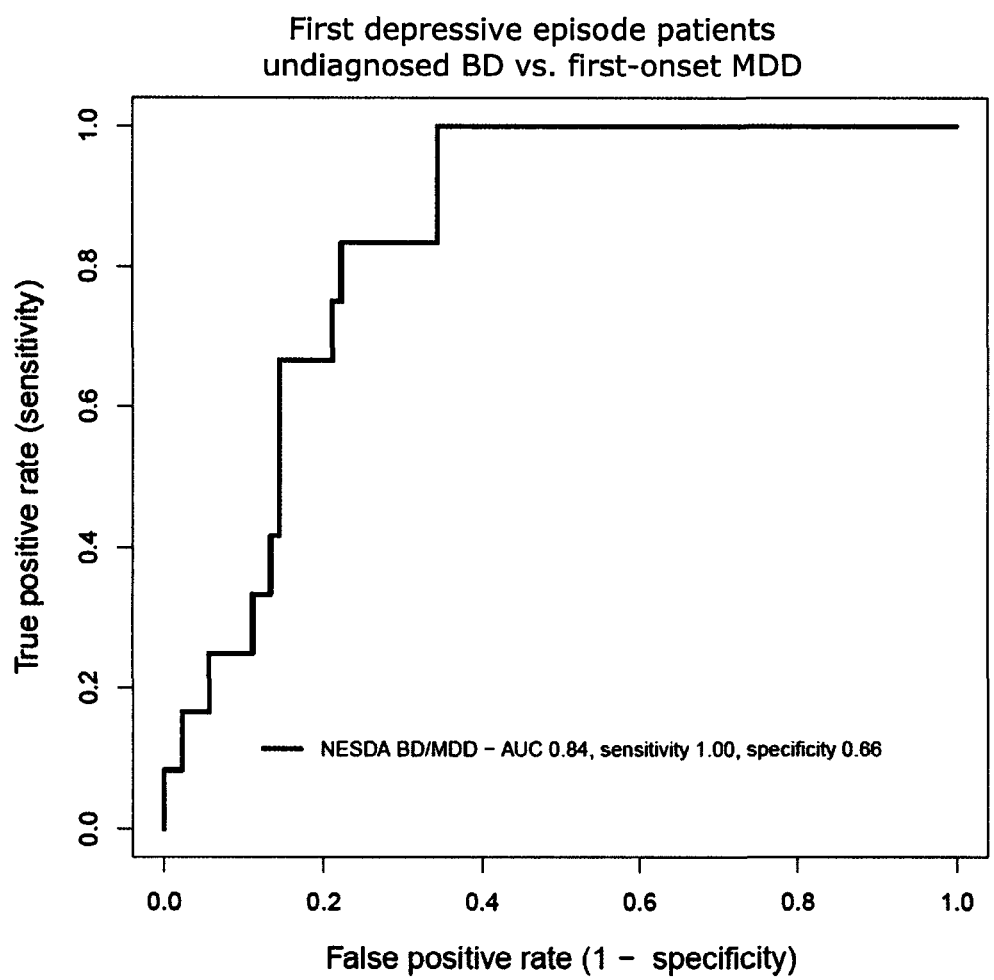
Figure 1C:
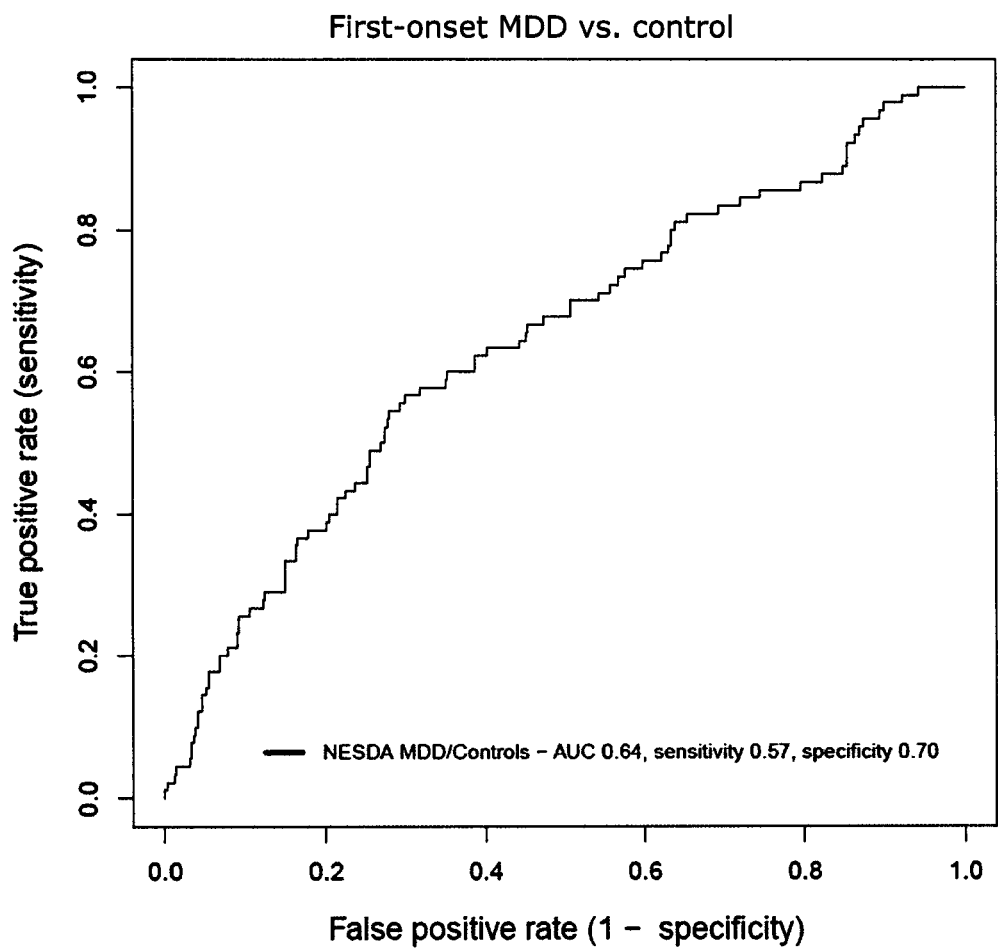
Figure 1D:
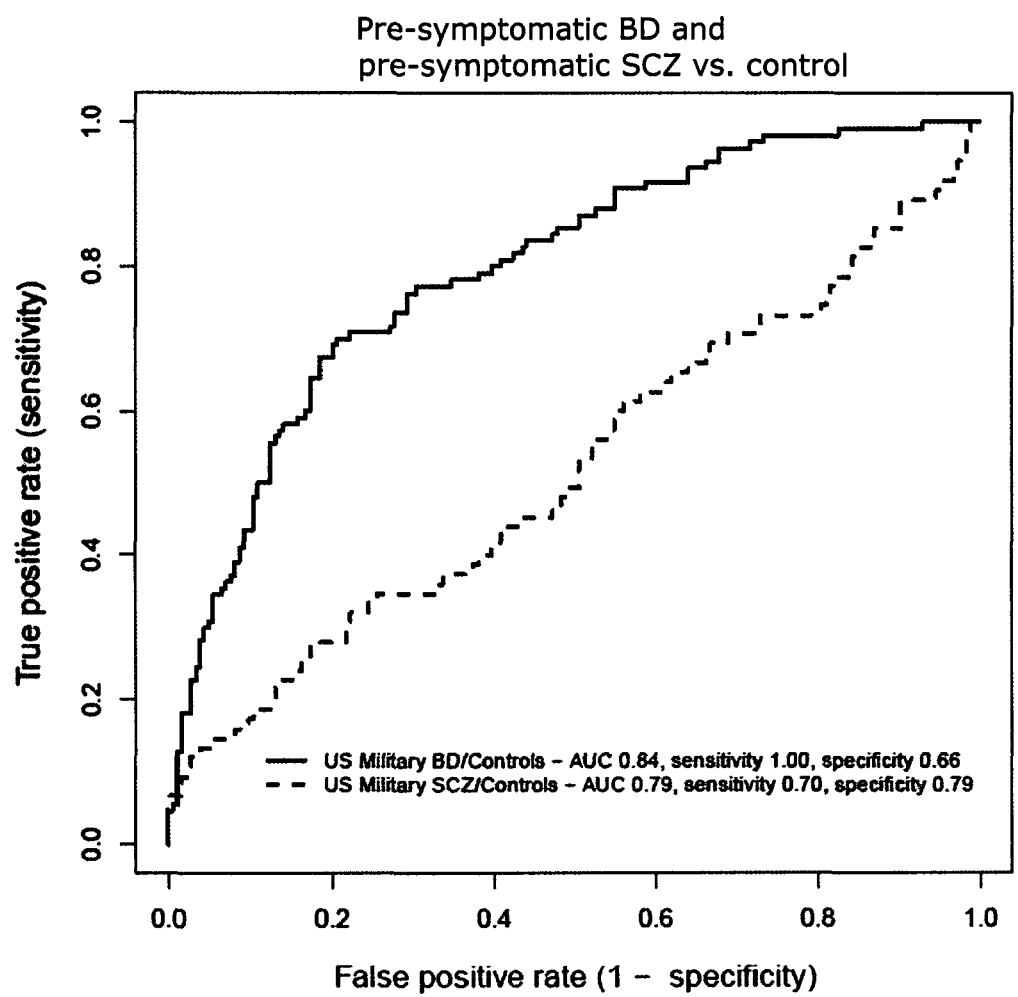
Figure 1E:
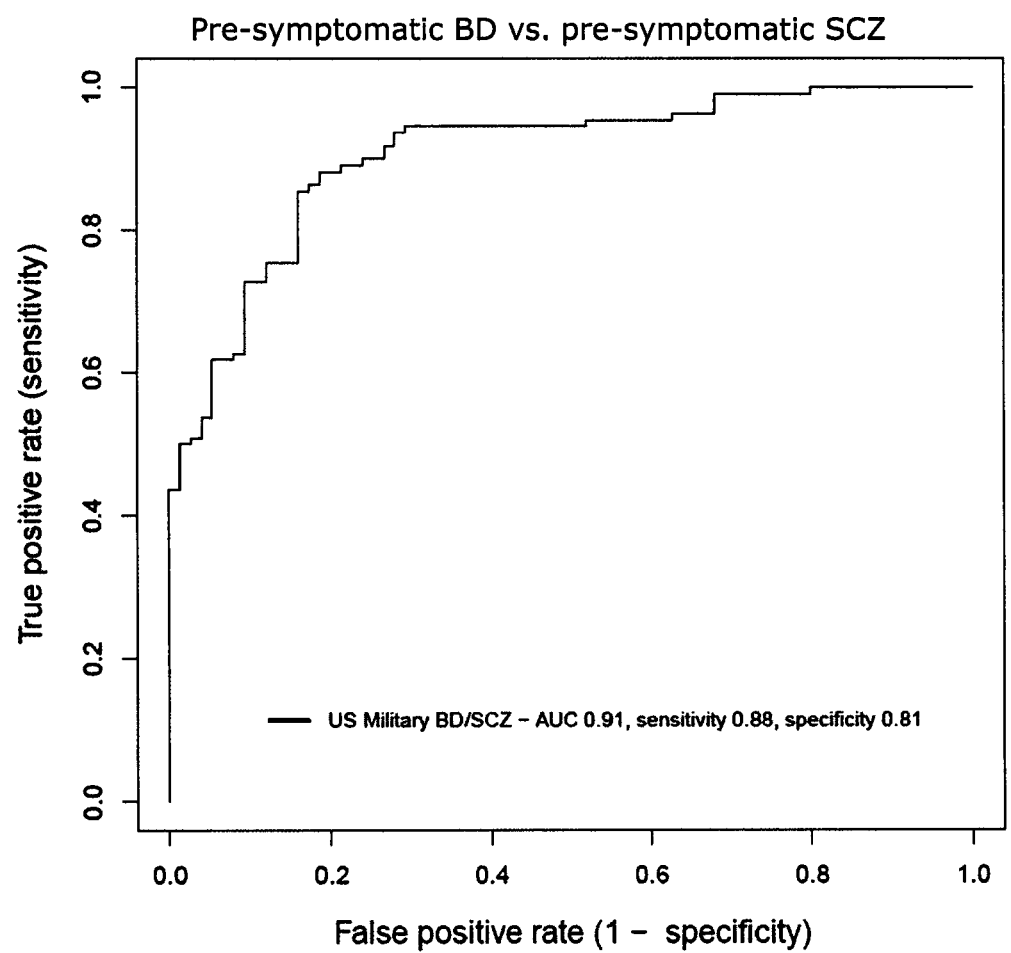
Figure 1F:
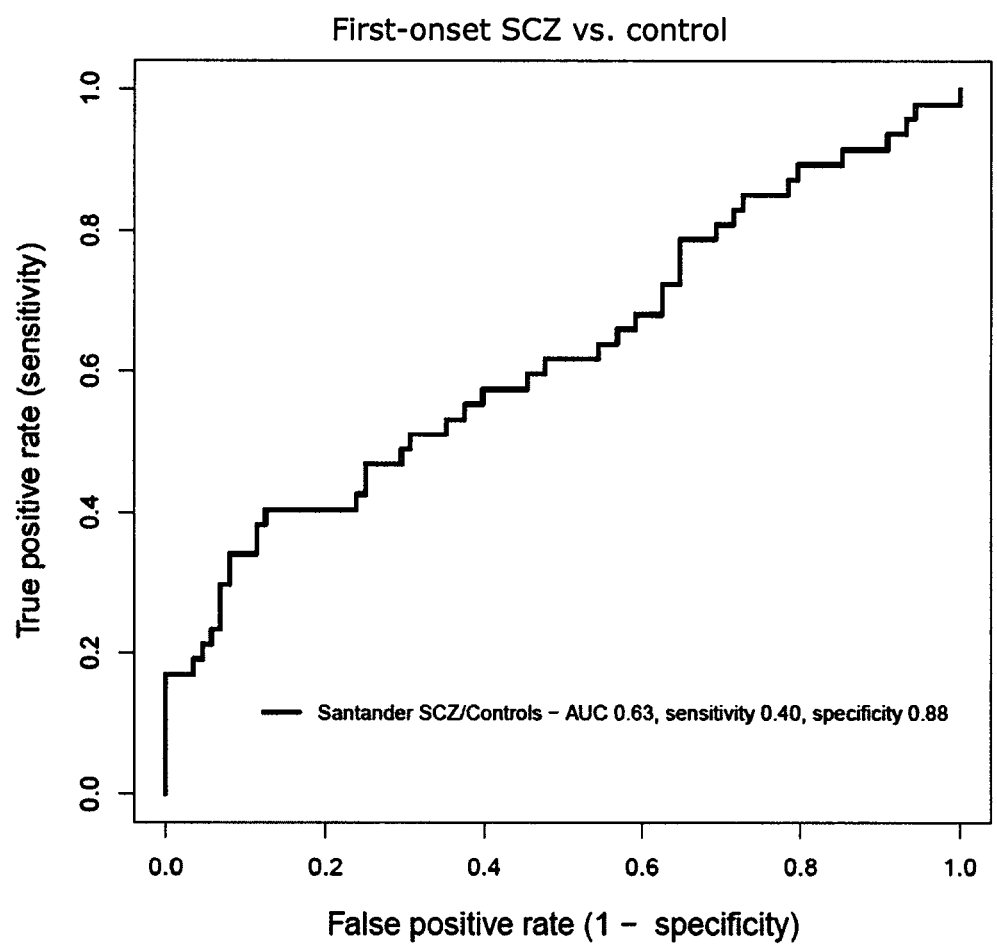

In this stage, the diagnostic performance of the biomarker panel was tested on undiagnosed BD patients and tested the disease specificity of the panel. It is important to note that the patient samples used in the application stage were collected at an earlier time point in the course of disease compared to the established BD patients used in the discovery and validation stages. Given the overlapping presentations of MDD and BD (FIG. 1), and the implications of misdiagnosis, the need for a diagnostic test to distinguish between the two conditions is clear. To this end, the predictive performance of the panel was tested on 102 first onset "MDD patients" including 12 individuals who later developed BD selected from the NESDA cohort. All of the 12 misdiagnosed BD patients experienced a manic or hypomanic episode within two years of the baseline blood sample collection and clinical interview. Using the panel, a good predictive performance (AUC=0.84; FIG. 1B) to differentiate between these two patient groups was obtained, but were limited to 18 of the 20 analytes forming the panel (see Table 2). In addition, to test the differential diagnostic utility of the biomarker panel, the fitted model from the analysis of first onset MDD and misdiagnosed BD patients was applied to differentiate between 90 first onset MDD patients, the first onset MDD patients from NESDA who did not develop BD, and 368 controls. Importantly, the predictive performance of the biomarker panel for first onset MDD patients was poor (AUC=0.64; FIG. 1C). The predictive performance of the biomarker panel in pre-symptomatic BD patients (FIG. 1) was then tested. The diagnostic panel was applied to 110 pre-symptomatic BD patients and 184 controls from the USA Military, where patients presented with initial psychiatric symptoms within 30 days of the blood test and later obtained a diagnosis of BD. The predictive performance was fair (AUC=0.79; FIG. 1D), but bordering the AUC threshold for a good predictive performance. One of the 20 analytes forming the biomarker panel was not available (see Table 2). As 75 pre-symptomatic SCZ patients from the USA Military, which underwent protein profiling and were pre-processed (including ComBat adjustment) at the same time, it was tested whether the biomarker panel could differentiate between the pre-symptomatic BD and SCZ patient groups. The predictive performance was excellent (AUC=0.91; FIG. 1E). To test the specificity of the biomarker panel, the fitted model from the analysis of pre-symptomatic BD patients and controls was applied to differentiate between pre-symptomatic SCZ patients and controls. Importantly, the predictive performance was almost equivalent to "tossing a coin" (AUC=0.52; classification description 'fair'; FIG. 1D). The excellent BD specificity of the panel was also reproduced in a further cohort of 47 drug-naïve, first-onset SCZ patients and 88 controls from the Santander study (AUC=0.63; FIG. 1F). In this analysis, the model was fitted using the analyte data from the Würzburg validation study, which underwent profiling and pre-processing (including ComBat adjustment) at the same time, and applied the fitted model to the Santander analyte data. The study was limited to 16 of the 20 analytes forming the panel available in the Würzburg validation study (see Table 2).

Discussion

To date, despite the established clinical need for a diagnostic test for BD to be routinely used in conjunction with a clinical interview, on-going research has as yet not provided the basis for a diagnostic test with clinical utility. Previous proteomics based approaches have tended to report single analytes[33]. In the present study, one of the largest diagnostic biomarker studies for BD, it has been demonstrated for the first time the potential of a biomarker panel to provide a blood-based diagnostic test for BD.

Figure 2:
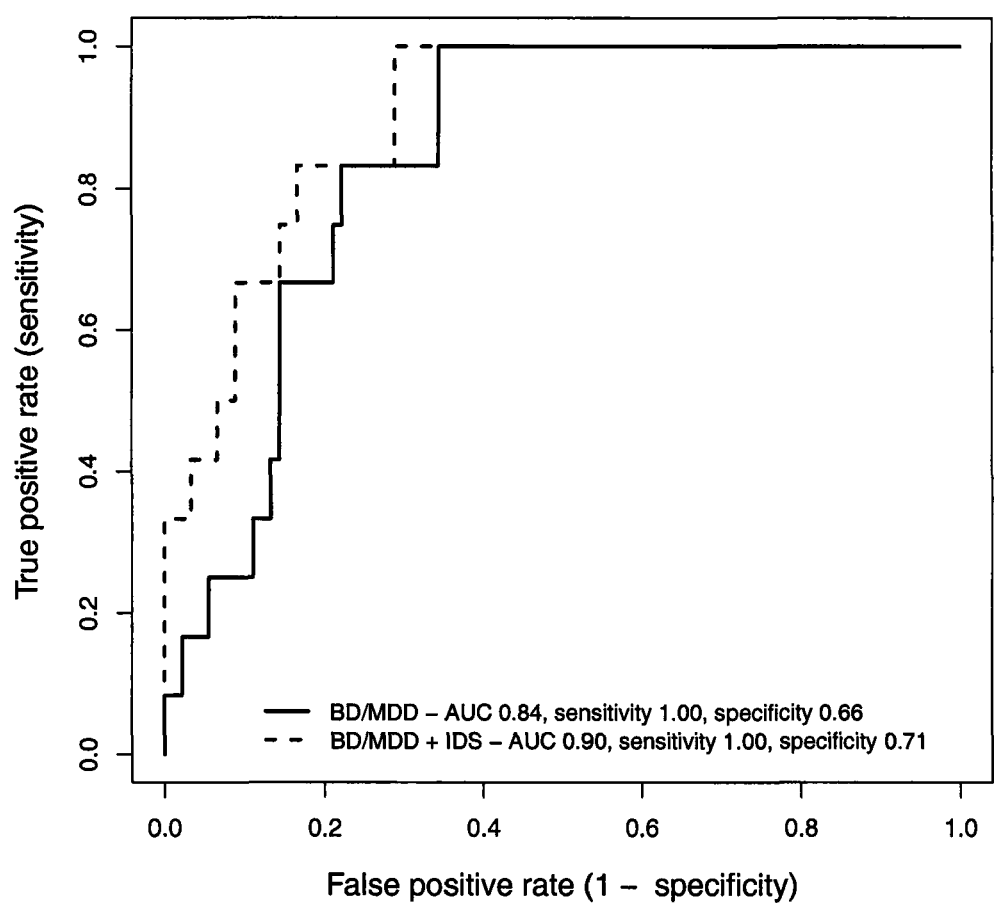
FIG. 2: ROC curves for the application of the diagnostic biomarker panel to the NESDA cohort. The BD panel was applied to first onset MDD patients that included patients who were later diagnosed with bipolar disorder (AUC=0.84, solid line). Then, the logistic regression model was expanded to include IDS score as a covariate (AUC=0.90, dashed line).

Given the insidious onset and that most BD patients initially present with depressive symptoms, the most appropriate time for a routine diagnostic test for BD would be when individuals present with a first depressive episode. Although this study defined and validated the diagnostic biomarker panel in established BD patients and controls, when this panel was applied to differentiate between first onset MDD patients and individuals who later develop hypomanic or manic symptoms, a good predictive performance (AUC=0.84) was obtained. As first onset MDD patients were recruited within the NESDA study, extensive clinical and rating scale information of participants was collected. When relevant rating scale variables were included in the analysis, the addition of either the Inventory of Depressive Symptomatology (IDS) or Beck Anxiety Inventory (BAI) scores led to an increase in the test performance to excellent levels for the prediction of first onset "MDD patients" who later develop BD (AUC=0.90; FIG. 2). Testing first onset "MDD patients" with a blood-based biomarker test has the potential to identify most BD patients before their first (hypo)manic episode. This will reduce the delay between the initial presentation of clinical symptoms, correct diagnosis and increase the chance of effective treatment before a first (hypo)manic episode, which in turn has the potential to delay or even avert the onset of BD.

The biomarker panel was also tested in pre-symptomatic BD patients and controls (AUC=0.79), and demonstrated the differential diagnostic utility of the panel when applied to first onset MDD patients and controls (AUC=0.64); pre-symptomatic SCZ patients and controls (AUC=0.52); or first onset, drug-naïve SCZ patients and controls (AUC=0.63). Furthermore, and as expected, this study was able to demonstrate that the panel could differentiate between pre-symptomatic BD patients and pre-symptomatic SCZ patients (AUC=0.91). We have also checked for common analytes in published MDD[34] and SCZ[20] diagnostic biomarker panels. We found no biomarkers in common between the BD panel of the invention and a commercially used MDD panel of nine biomarkers. Only three biomarkers (CD40, IL-10 and carcinoembryonic antigen) overlap between our BD and the published SCZ panel of 34 biomarkers[20].

The molecular mechanisms of the selected analytes, which can distinguish BD patients in different disease stages (pre-symptomatic, first depressive episode and established patients), reveal new insights into the progressive nature of BD. Importantly, amongst the 20 analyte BD panel, 3 analytes (Matrix-metalloproteinase-3 (MMP-3), MMP-7 and MMP-9) belong to a structurally related family of secreted proteases that play an important role in extracellular matrix degradation[35]. Matrix-metalloproteinases (MMPs) have been implicated in the regulation of cell survival, angiogenesis, cell signalling and the maintenance of an intact blood-brain barrier. Alterations in serum levels of several MMPs have been reported for neurodegenerative and neuroinflammatory diseases like Alzheimer's disease[36], multiple sclerosis (MS)[37], meningitis[38] and cerebral stroke[39].

Overexpression of MMPs, including MMPs secreted by T-cells and macrophages, are known to damage and open the blood brain barrier[40,41,42]. MMP-3, -7 and -9 expression is increased in astrocytes, microglia and neurons surrounding white matter lesions in MS[43,44]. MMP-9 expression levels in brain tissue of MS patients were reported to be correlated with increased serum levels[37]. White matter hyperintensities in BD patients are a reproducible finding in imaging studies[45]. The present study found increased levels of MMP-9 and -7 in serum from BD patients, while MMP-3 levels were decreased. Interestingly, MS patients have a significantly higher risk to develop BD than controls[46,47]. MMP-7 and MMP-9 play a key role in the conversion of pro brain-derived neutrotrophic factor (BDNF) into mature BDNF in the extracellular matrix[48,49]. Serum MMP-9 levels have previously been reported to be positively correlated with levels of mature BDNF in BD patients[50]. BDNF is an important neurotrophin, which can readily cross the blood-brain barrier. Accumulating evidence suggests that BDNF is critically involved in the pathogenesis of BD[51]. In addition to MMPs, antipsychotic treatment might further contribute to the blood-brain barrier dysfunction[52].

Over half of the analytes (11/20) in the panel were associated with inflammatory response. The majority of these analytes have a pro-inflammatory role and the remaining three have an anti-inflammatory role (see Table 4). Levels of five of the eight pro-inflammatory analytes (Carcinoembryonic Antigen, EN-RAGE, Macrophage Inflammatory Protein-1 beta, Receptor for advanced glycosylation end products, Serum Amyloid P-Component, Tumor Necrosis Factor Receptor-Like 2) were increased and in addition, one of the anti-inflammatory analytes (CD5) was found to be decreased in BD patients. Consequently, proteins promoting pro-inflammatory processes are predominant in BD serum. These findings are consistent with previous reports[53].

A third functional group of changing serum proteins in BD relate to decreased levels of Apolipoprotein A1 and A2 and increased levels of Lipoprotein (a), which facilitate cholesterol and triglyceride transport, but also play a role in regulation of inflammation[54]. Decreased levels of Apolipoprotein-A1 have been found in serum and cerebrospinal fluid of patients suffering from a wide range of neurodegenerative disorders[54], stroke[55] and schizophrenia[56]. Changes in lipid metabolism are also consistent with an increased risk for cardiovascular events in BD[57]. Amongst all comorbities in BD, the main cause of death is mortality related to cardiovascular disease[58], thus supporting the understanding of BD as a multi-system inflammatory disease, as proposed in recent literature[59].

There are several limitations to the present study. As age and sex were the only covariates available across the eight case-control studies used in the meta-analysis, the present study identified a diagnostic test without considering the incorporation of other relevant clinical variables, for example, symptom scores. When additional clinical variables are considered in the nested case-control study from NESDA, the selection of certain rating scale-derived symptom scores improved the predictive performance of the panel (see above). It is anticipated that the addition of clinical variables to the biomarker panel will improve the predictive performance. Of all the studies analysed, the most relevant for a diagnostic test was the nested study from the NESDA cohort, which included first onset "MDD patients" who later developed (hypo)manic symptoms. However, of the 102 first onset "MDD patients" diagnosed at baseline, only 12 patients were diagnosed as having BD within two years of assessment. More prospective studies with a larger number of first onset MDD patients and long-term follow-up will be required to develop and establish a blood-based diagnostic biomarker test.

In conclusion, the 20 analytes of the invention, represent a preliminary panel of validated biomarkers from which a definitive signature for the diagnosis and prognosis of BD in the clinical setting could be developed. The ultimate goal will be to implement a low-cost blood test that can be routinely used in primary and secondary clinical care settings in conjunction with a clinical interview for the diagnosis of BD before the development of hypomanic or manic symptoms.

Example 2: Identification of Core Diagnostic Biomarker Panels for Bipolar Disorder The study described in Example 1 resulted in the identification of a 20 biomarker panel for bipolar disorder.

This study involved the definition of 'core' biomarker panels for the diagnosis of bipolar disorder which retained the majority of the statistical significance observed with the 20 biomarker panel.

Firstly, a "six" biomarker panel comprising: CD5; Growth-Regulated alpha protein; Matrix Metalloprotease-3; Matrix Metalloprotease-7; Serum Amyloid P-component; and Tumor Necrosis Factor Receptor-Like 2 was tested for sensitivity and specificity and the results are shown in Tables 5 and 6 and FIGS. 3 to 5 where good results were obtained for specificity and sensitivity with the six biomarker panel.

Secondly, a "seven" biomarker panel comprising: CD5; Growth-Regulated alpha protein; Matrix Metalloprotease-3; Matrix Metalloprotease-7; Serum Amyloid P-component; Tumor Necrosis Factor Receptor-Like 2; and CD40 ligand was tested for sensitivity and specificity and the results are shown in Tables 5 and 6 and FIGS. 3 to 5 where good results were obtained for specificity and sensitivity with the seven biomarker panel. In particular, the seven biomarker panel improved the results observed for the six biomarker panel in recent onset major depressive disorder (MDD) patients from NESDA, which included patients that developed BD within two years.

Finally, an "nine" biomarker panel comprising: CD5; Growth-Regulated alpha protein; Matrix Metalloprotease-3; Matrix Metalloprotease-7; Serum Amyloid P-component; Tumor Necrosis Factor Receptor-Like 2; CD40 ligand; Apolipoprotein A1; and Apolipoprotein A2 was tested for sensitivity and specificity and the results are shown in Tables 5 and 6 and FIGS. 3 to 5 where good results were obtained for specificity and sensitivity with the nine biomarker panel. In particular, the nine biomarker panel improved the results observed for the seven biomarker panel in pre-symptomatic bipolar disorder patients and controls from the USA Military. Consequently, the nine biomarker panel represents a particularly preferred core biomarker panel of the invention.

TABLE 5

The area under the receiver operating characteristic (ROC) curves (AUC) for the predictive performance of the core biomarker panels in the discovery, validation and application case-control studies

| | | Reduced panel | | |
|---|---|---|---|---|
| Stage Study | Type | 6 biomarkers | 7 biomarkers | 9 biomarkers |
| | | Discovery: | | |
| Meta-analysis | BD/Controls | 0.85 | 0.86 | 0.87 |
| | | Validation: | | |
| ⸰Würzburg | BD/Controls | 0.87 | 0.87 | 0.89 |
| | | Application: | | |
| NESDA | BD/MDD (+IDS) | 0.63 (0.78) | 0.77 (0.86) | 0.80 (0.87) |
| | MDD/Controls | 0.57 | 0.57 | 0.58 |

TABLE 5-continued

The area under the receiver operating characteristic (ROC) curves (AUC) for the predictive performance of the core biomarker panels in the discovery, validation and application case-control studies

| Stage Study | Type | Reduced panel | | |
|---|---|---|---|---|
| | | 6 biomarkers | 7 biomarkers | 9 biomarkers |
| USA Military | BD/Controls | 0.63 | 0.63 | 0.75 |
| | SCZ/Controls | 0.48 | 0.48 | 0.43 |
| | BD/SCZ | 0.71 | 0.71 | 0.87 |
| ∓Santander | SCZ/Controls | 0.59 | 0.57 | 0.64 |

∓Growth-Regulated alpha protein not available in Würzburg and not used in Santander as the prediction was based on the Würzburg fitted model. "+IDS" = Inventory of Depressive Symptomatology score was included in the model with the biomarker panel.

TABLE 6

The sensitivity for the core biomarker panels for the discovery, validation and application case-control studies. Optimal trade-offs between sensitivity and specificity were determined by maximising Youden's index (J; where J = sensitivity + specificity − 1)

| Stage Study | Type | Reduced panel | | |
|---|---|---|---|---|
| | | 6 biomarkers | 7 biomarkers | 9 biomarkers |
| | | Discovery: | | |
| Meta-analysis | BD/Controls | 0.77 | 0.72 | 0.75 |
| | | Validation: | | |
| ∓Würzburg | BD/Controls | 0.80 | 0.86 | 0.83 |
| | | Application: | | |
| NESDA | BD/MDD | 0.83 | 0.83 | 0.83 |
| | (+IDS) | (0.83) | (0.83) | (1.00) |
| | MDD/Controls | 0.57 | 0.57 | 0.53 |
| USA Military | BD/Controls | 0.68 | 0.63 | 0.75 |
| | SCZ/Controls | 0.093 | 0.080 | 0.11 |
| | BD/SCZ | 0.70 | 0.70 | 0.75 |
| ∓Santander | SCZ/Controls | 0.55 | 0.49 | 0.72 |

∓Growth-Regulated alpha protein not available in Würzburg and not used in Santander as the prediction was based on the Würzburg fitted model. "+IDS" = Inventory of Depressive Symptomatology score was included in the model with the biomarker panel.

LIST OF REFERENCES

1. Paykel, E. Manic-Depressive Illness: Bipolar Disorders and Recurrent Depression (2nd edn). *Br. J. Psychiatry* 193, 86-87 (2008).
2. Merikangas, K. R. et al. Lifetime and 12-month prevalence of bipolar spectrum disorder in the National Comorbidity Survey replication. *Arch. Gen. Psychiatry* 64, 543-552 (2007).
3. Müller-Oerlinghausen, B., Berghöfer, A. & Bauer, M. Bipolar disorder. *Lancet* 359, 241-247 (2002).
4. Goldstein, B. I., Fagiolini, A., Houck, P. & Kupfer, D. J. Cardiovascular disease and hypertension among adults with bipolar I disorder in the United States. *Bipolar Disord.* 11, 657-62 (2009).
5. Kilbourne, A. M. et al. Burden of general medical conditions among individuals with bipolar disorder. *Bipolar Disord.* 6, 368-73 (2004).
6. Leon, A. C. et al. Risk of suicidal behavior with antidepressants in bipolar and unipolar disorders. *J. Clin. Psychiatry* 75, 720-7 (2014).
7. Wittchen, H. U. et al. The size and burden of mental disorders and other disorders of the brain in Europe 2010. *Eur. Neuropsychopharmacol.* 21, 655-79 (2011).
8. Olesen, J., Gustaysson, a, Svensson, M., Wittchen, H.-U. & Jönsson, B. The economic cost of brain disorders in Europe. *Eur. J. Neurol.* 19, 155-62 (2012).
9. Ghaemi, S. N., Sachs, G. S., Chiou, A. M., Pandurangi, A. K. & Goodwin, K. Is bipolar disorder still underdiagnosed? Are antidepressants overutilized? *J. Affect. Disord.* 52, 135-44
10. Colom, F., Vieta, E., Daban, C., Pacchiarotti, I. & Sanchez-Moreno, J. Clinical and therapeutic implications of predominant polarity in bipolar disorder. *J. Affect. Disord.* 93, 13-17 (2006).
11. Vieta, E. et al. Predominant previous polarity as an outcome predictor in a controlled treatment trial for depression in bipolar I disorder patients. *J. Affect. Disord.* 119, 22-7 (2009).
12. Colom, F. & Vieta, E. The road to DSM-V. Bipolar disorder episode and course specifiers. Psychopathology 42, 209-218 (2009).
13. Hirschfeld, R. M. A., Lewis, L. & Vornik, L. A. Perceptions and impact of bipolar disorder: how far have we really come? Results of the national depressive and manic-depressive association 2000 survey of individuals with bipolar disorder. *J. Clin. Psychiatry* 64, 161-174 (2003).
14. Schwarz, E. et al. Biomarkers for Psychiatric Disorders. *Sci. York* 75-96 (2009). doi:10.1007/978-0-387-79251-4
15. Schwarz, E. & Bahn, S. Biomarker discovery in psychiatric disorders. Electrophoresis 29, 2884-2890 (2008).
16. Bragazzi, N. L. Rethinking psychiatry with OMICS science in the age of personalized P5 medicine: ready for psychiatome? *Philos. Ethics. Humanit. Med.* 8, 4 (2013).
17. Atluri, G. et al. Complex biomarker discovery in neuroimaging data: Finding a needle in a haystack. *NeuroImage. Clin.* 3, 123-31 (2013).
18. Craddock, N. & Sklar, P. Genetics of bipolar disorder. *Lancet* 381, 1654-62 (2013).
19. Schwarz, E. et al. Biomarker Insights Validation of a Blood-Based Laboratory Test to Aid in the Confirmation of a Diagnosis of Schizophrenia. *Biomark. Insights* 12, 39-47 (2010).
20. Schwarz, E. et al. Identification of a biological signature for schizophrenia in serum. *Mol. Psychiatry* (2011). doi: 10.1038/mp.2011.42
21. Niebuhr, D. W. et al. Association between bovine casein antibody and new onset schizophrenia among US military personnel. *Schizophr. Res.* 128, 51-55 (2011).
22. Millikan, A. M. et al. Evaluation of data obtained from military disability medical administrative databases for service members with schizophrenia or bipolar disorder. *Mil. Med.* 172, 1032-1038 (2007).
23. Penninx, B. W. J. H. et al. The Netherlands Study of Depression and Anxiety (NESDA): rationale, objectives and methods. 17, 121-140 (2008).
24. Pelayo-Terán, J. M. et al. Epidemiological factors associated with treated incidence of first-episode non-affective psychosis in Cantabria: insights from the Clinical Programme on Early Phases of Psychosis. *Early Interv. Psychiatry* 2, 178-87 (2008).
25. Bertenshaw, G. P. et al. Multianalyte Profiling of Serum Antigens and Autoimmune and Infectious Disease Molecules to Identify Biomarkers Dysregulated in Epithelial Ovarian Cancer. *Cancer Epidemiol. Biomarkers Prev.* 17, 2872-2881 (2008).

26. R Core Team. *R: A Language and Environment for Statistical Computing.* R Found. Stat. Comput. Vienna, Austria http://www.R-project.org (2014).
27. Vic Barnett, T. L. Outliers in Statistical Data. 608 (Wiley-blackwell publishing, inc, 1994).
28. Schwarz, E. et al. Identification of a blood-based biological signature in subjects with psychiatric disorders prior to clinical manifestation. *world J. Biol. psychiatry* article in, (2011).
29. Johnson, W. E., Li, C. & Rabinovic, A. Adjusting batch effects in microarray expression data using empirical Bayes methods. *Biostatistics* 8, 118-127 (2007).
30. Leek, J. T., Johnson, W. E., Parker, H. S., Jaffe, A. E. & Storey, J. D. The SVA package for removing batch effects and other unwanted variation in high-throughput experiments. *Bioinformatics* 28, 882-883 (2012).
31. Friedman, J., Hastie, T. & Tibshirani, R. Regularization Paths for Generalized Linear Models via Coordinate Descent. *J. Stat. Softw.* 33, 1-22 (2010).
32. Gareth James, Daniela Witten, Trevor Hastie, R. T. *An Introduction to Statistical Learning: with Applications in R.* 426 (Springer, 2013).
33. Chan, M. K. et al. Applications of blood-based protein biomarker strategies in the study of psychiatric disorders. *Prog. Neurobiol.* (2014). doi:10.1016/j.pneurobio.2014.08.002
34. Papakostas, G. I. et al. Assessment of a multi-assay, serum-based biological diagnostic test for major depressive disorder: a pilot and replication study. *Mol. Psychiatry* 18, 332-9 (2013).
35. Chopra, K., Baveja, A. & Kuhad, A. MMPs: a novel drug target for schizophrenia. *Expert Opin. Ther. Targets* 1-9 (2014). doi:10.1517/14728222.2014.957672
36. Romi, F., Helgeland, G. & Gilhus, N. E. Serum levels of matrix metalloproteinases: implications in clinical neurology. *Eur. Neurol.* 67, 121-8 (2012).
37. Waubant, E. et al. Serum MMP-9 and TIMP-1 levels are related to MRI activity in relapsing multiple sclerosis. *Neurology* 53, 1397-401 (1999).
38. Tsai, H.-C. et al. Expression of matrix metalloproteinases and their tissue inhibitors in the serum and cerebrospinal fluid of patients with meningitis. *Clin. Microbiol. Infect.* 17, 780-4 (2011).
39. Ning, M. et al. Association between tPA therapy and raised early matrix metalloproteinase-9 in acute stroke. *Neurology* 66, 1550-5 (2006).
40. Chopra, K., Baveja, A. & Kuhad, A. MMPs: a novel drug target for schizophrenia. *Expert Opin. Ther. Targets* 1-9 (2014). doi:10.1517/14728222.2014.957672
41. Leppert, D., Waubant, E., Galardy, R., Bunnett, N. W. & Hauser, S. L. T cell gelatinases mediate basement membrane transmigration in vitro. *J. Immunol.* 154, 4379-89 (1995).
42. Rosenberg, G. A. et al. TIMP-2 reduces proteolytic opening of blood-brain barrier by type IV collagenase. *Brain Res.* 576, 203-7 (1992).
43. Cossins, J. A. et al. Enhanced expression of MMP-7 and MMP-9 in demyelinating multiple sclerosis lesions. *Acta Neuropathol.* 94, 590-8 (1997).
44. Maeda, A. & Sobel, R. A. Matrix metalloproteinases in the normal human central nervous system, microglial nodules, and multiple sclerosis lesions. *J. Neuropathol. Exp. Neurol.* 55, 300-9 (1996).
45. De Peri, L. et al. Brain structural abnormalities at the onset of schizophrenia and bipolar disorder: a meta-analysis of controlled magnetic resonance imaging studies. *Curr. Pharm. Des.* 18, 486-94 (2012).
46. Carta, M. G. et al. The risk of Bipolar Disorders in Multiple Sclerosis. *J. Affect. Disord.* 155, 255-60 (2014).
47. Ybarra, M. I., Moreira, M. A., Araújo, C. R., Lana-Peixoto, M. A. & Teixeira, A. L. Bipolar disorder and multiple sclerosis. *Arq. Neuropsiquiatr.* 65, 1177-80 (2007).
48. Anastasia, A. et al. Val66Met polymorphism of BDNF alters prodomain structure to induce neuronal growth cone retraction. *Nat. Commun.* 4, 2490 (2013).
49. Lu, B. Pro-region of neurotrophins: Role in synaptic modulation. Neuron 39, 735-738 (2003).
50. Södersten, K. et al. Abnormality in serum levels of mature brain-derived neurotrophic factor (BDNF) and its precursor proBDNF in mood-stabilized patients with bipolar disorder: a study of two independent cohorts. *J. Affect. Disord.* 160, 1-9 (2014).
51. Hashimoto, K. Brain-derived neurotrophic factor as a biomarker for mood disorders: an historical overview and future directions. *Psychiatry Clin. Neurosci.* 64, 341-57 (2010).
52. Zetterberg, H. et al. Blood-cerebrospinal fluid barrier dysfunction in patients with bipolar disorder in relation to antipsychotic treatment. *Psychiatry Res.* 217, 143-6 (2014).
53. Kim, Y. K., Jung, H. G., Myint, A. M., Kim, H. & Park, S. H. Imbalance between pro-inflammatory and anti-inflammatory cytokines in bipolar disorder. *J. Affect. Disord.* 104, 91-95 (2007).
54. Keeney, J. T. R. et al. Apolipoprotein A-I: insights from redox proteomics for its role in neurodegeneration. *Proteomics. Clin. Appl.* 7, 109-22 (2013).
55. As, S., Sahukar, S., Murthy, J. & Kumar, K. A study of serum apolipoprotein A1, apolipoprotein B and lipid profile in stroke. *J. Clin. Diagn. Res.* 7, 1303-6 (2013).
56. Huang, J. T.-J. et al. Independent protein-profiling studies show a decrease in apolipoprotein A1 levels in schizophrenia CSF, brain and peripheral tissues. *Mol. Psychiatry* 13, 1118-28 (2008).
57. Lakka, H.-M. et al. The metabolic syndrome and total and cardiovascular disease mortality in middle-aged men. *JAMA* 288, 2709-16 (2002).
58. McElroy, S. L. & Keck, P. E. Metabolic syndrome in bipolar disorder: a review with a focus on bipolar depression. *J. Clin. Psychiatry* 75, 46-61 (2014).
59. Leboyer, M. et al. Can bipolar disorder be viewed as a multi-system inflammatory disease? *J. Affect. Disord.* 141, 1-10 (2012).

The invention claimed is:
1. A method of treating a bipolar disorder patient, comprising:
administering a bipolar disorder medicament to a patient identified as having differing levels of a panel of biomarkers when compared to the levels of said biomarkers from a normal subject,
wherein the panel of biomarkers comprises CD5, Growth-Regulated alpha protein, Matrix Metalloproteinase-3, Matrix Metalloproteinase-7, Serum Amyloid P-component, and Tumor Necrosis Factor Receptor-Like 2,
the bipolar disorder patient has a higher level of Matrix Metalloproteinase-7, Serum Amyloid P-component and Tumor Necrosis Factor Receptor-Like 2 than the normal subject, and
the bipolar disorder patient has a lower level of CD5, Growth-Regulated alpha protein and Matrix Metalloproteinase-3 than the normal subject.
2. The method of claim 1, wherein the panel of biomarkers further comprises CD40 ligand.

3. The method of claim 2, wherein the panel of biomarkers further comprises Apolipoprotein A1 and Apolipoprotein A2.

4. The method of claim 3, wherein the panel of biomarkers further comprises Angiotensin-Converting Enzyme, Carcinoembryonic Antigen, Cystatin C, EN-RAGE, Hepatocyte Growth Factor, Interleukin-10, Interleukin-1 receptor antagonist, Lipoprotein (a), Macrophage Inflammatory Protein-1 beta, Matrix Metalloproteinase-9, total, and Receptor for advanced glycation end-products.

5. The method of claim 1, wherein the bipolar disorder patient is a first-onset drug-nave patient.

6. A method of treating an individual, comprising:
(a) quantifying the amounts of a panel of biomarkers in a biological sample obtained from the individual;
(b) comparing the amounts of the biomarkers in the biological sample with the amounts present in a normal control biological sample from a normal subject, such that a difference in the level of the biomarkers in the biological sample is indicative of bipolar disorder, or predisposition thereto; and
(c) administering a bipolar disorder medicament to the individual when the level of the biomarkers in the biological sample is indicative of bipolar disorder or predisposition thereto;
wherein the panel of biomarkers comprises CD5, Growth-Regulated alpha protein, Matrix Metalloproteinase-3, Matrix Metalloproteinase-7, Serum Amyloid P-component, and Tumor Necrosis Factor Receptor-Like 2, and
the level of the biomarkers in the biological sample is indicative of bipolar disorder or predisposition thereto when there is a higher level of Matrix Metalloproteinase-7, Serum Amyloid P-component and Tumor Necrosis Factor Receptor-Like 2 and a lower level of CD5, Growth-Regulated alpha protein and Matrix Metalloproteinase-3 as compared to the normal control biological sample from the normal subject.

7. The method of claim 6, wherein the quantifying comprises obtaining biological samples taken on two or more occasions from the individual.

8. The method of claim 6, wherein the biological sample is obtained prior to therapy for bipolar disorder.

9. The method of claim 6, wherein the biological sample is obtained during therapy for bipolar disorder.

10. The method of claim 6, wherein the biological sample is obtained following therapy for bipolar disorder.

11. The method of claim 6, wherein the quantifying comprises measuring the concentration of the biomarkers in the biological sample.

12. The method of claim 6, wherein the quantifying comprises SELDI (-TOF) or MALDI (-TOF).

13. The method of claim 6, wherein the quantifying comprises an immunological method.

14. The method of claim 6, wherein the quantifying is performed using a biosensor.

15. The method of claim 6, wherein the biological sample comprises blood.

16. The method of claim 6, wherein the biological sample comprises whole blood, blood serum, or plasma.

17. The method of claim 6, wherein the panel of biomarkers further comprises CD40 ligand.

18. The method of claim 17, wherein the panel of biomarkers further comprises Apolipoprotein A1 and Apolipoprotein A2.

19. The method of claim 18, wherein the panel of biomarkers further comprises Angiotensin-Converting Enzyme, Carcinoembryonic Antigen, Cystatin C, EN-RAGE, Hepatocyte Growth Factor, Interleukin-10, Interleukin-1 receptor antagonist, Lipoprotein (a), Macrophage Inflammatory Protein-1 beta, Matrix Metalloproteinase-9, total, and Receptor for advanced glycation end-products.

20. The method of claim 6, wherein the individual is a first-onset drug-nave individual.

* * * * *